United States Patent
Loh et al.

(10) Patent No.: US 12,156,725 B2
(45) Date of Patent: Dec. 3, 2024

(54) SMART ELASTIC FABRIC TAPE FOR DISTRIBUTED SKIN STRAIN, MOVEMENT, AND MUSCLE ENGAGEMENT MONITORING

(71) Applicant: THE REGENTS OF THE UNIVERSITY OF CALIFORNIA, Oakland, CA (US)

(72) Inventors: Kenneth Loh, San Diego, CA (US); Yun-An Lin, San Diego, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 304 days.

(21) Appl. No.: 17/379,522

(22) Filed: Jul. 19, 2021

(65) Prior Publication Data
US 2022/0087565 A1    Mar. 24, 2022

Related U.S. Application Data

(60) Provisional application No. 63/053,404, filed on Jul. 17, 2020.

(51) Int. Cl.
*A61B 5/0536* (2021.01)
*A61B 5/00* (2006.01)

(52) U.S. Cl.
CPC .......... *A61B 5/0536* (2013.01); *A61B 5/6831* (2013.01); *A61B 2562/046* (2013.01)

(58) Field of Classification Search
CPC .............. A61B 5/0536; A61B 5/6831; A61B 2562/046; A61B 2562/0285; A61B 5/4566; A61B 5/4528; A61B 2562/125; A61B 2562/164; A61B 5/224; A61B 5/4571; A61B 5/458; A61B 5/4585; A61B 5/4595; A61B 2505/09
See application file for complete search history.

(56) References Cited

U.S. PATENT DOCUMENTS

| 2009/0121727 A1* | 5/2009 | Lynch | G01R 27/02 324/609 |
| 2019/0231267 A1* | 8/2019 | Oren | A61B 5/01 |

OTHER PUBLICATIONS

Yu Ra Jeong, etc, "A skin-attachable, stretchable integrated system based on liquid GaInSn for wireless human motion monitoring with multi-site sensing capabilities"; NPG Asia Materials (2017) (Year: 2017).*

(Continued)

*Primary Examiner* — Eric F Winakur
*Assistant Examiner* — Abid A Mustansir
(74) *Attorney, Agent, or Firm* — Sheppard, Mullin, Richter & Hampton LLP

(57) ABSTRACT

Systems and methods relating to a smart elastic fabric tape are disclosed. For example, a method may include interrogating a sensing mesh using an electrical impedance tomography (EIT) device, wherein the sensing mesh is affixed onto skin nearby a musculoskeletal (MSK) region of interest, wherein the sensing mesh comprises a nanocomposite thin film disposed on elastic fabric tape, and wherein the sensing mesh forms a geometrical pattern on the skin; generating, in real-time, EIT conductivity maps from interrogating the sensing mesh; and generating, in real time, strain distribution and strain directionality data of the MSK region of interest based on the EIT conductivity maps.

12 Claims, 22 Drawing Sheets

(56) References Cited

OTHER PUBLICATIONS

Yingjun Zhao et al, "Characterization of the spatial elastoresistivity of inkjet-printed carbon nanotube thin films"; Smart Mater. Struct. (2018) (Year: 2018).*

* cited by examiner

SMART ELASTIC FABRIC TAPE FOR DISTRIBUTED SKIN STRAIN, MOVEMENT, AND MUSCLE ENGAGEMENT MONITORING

CROSS-REFERENCE TO RELATED APPLICATIONS

This application claims priority to, and the benefit of, U.S. Provisional Patent Application Ser. No. 63/053,404 filed on Jul. 17, 2020 and titled "SMART KINESIOLOGY TAPE FOR DENSELY DISTRIBUTED HUMAN MOTION MONITORING," which is incorporated herein by reference in its entirety.

STATEMENT REGARDING FEDERALLY SPONSORED R&D

This invention was made with government support under Grant No. N00014-20-1-2329 awarded by the Office of Naval Research. The government has certain rights in the Invention.

TECHNICAL FIELD

The present disclosure relates generally to smart elastic fabric tape, and in particular, interrogating smart elastic fabric tape that forms a sensing mesh using an EIT device to measure musculoskeletal activity of a musculoskeletal region of interest.

BRIEF SUMMARY OF THE DISCLOSURE

Disclosed are systems and methods that relate to a smart elastic fabric tape. A method may include one or more steps. One step may include interrogating a sensing mesh using an electrical impedance tomography (EIT) device. The sensing mesh may be affixed onto skin nearby a musculoskeletal (MSK) region of interest. The sensing mesh may include a nanocomposite thin film disposed on elastic fabric tape. The sensing mesh may form a geometrical pattern on the skin. Another step may include generating, in real-time, EIT conductivity maps from interrogating the sensing mesh. Yet another step may include generating, in real time, strain distribution and strain directionality data of the MSK region of interest based on the EIT conductivity maps.

In embodiments, the MSK region of interest may include one or more of a bicep region, pectoral region, latissimus dorsi region, gastrocnemius region, quadricep region, ankle region, knee region, elbow region, back region, and neck region.

In embodiments, the nanocomposite thin-film may include one or more of a graphene nanosheet, carbon nanotube, carbon black, and silver nanoparticles.

In embodiments, the sensing mesh may include conductive threads, fibers, or wires electrically coupling edges of the sensing mesh together.

In embodiments, disposing the nanocomposite thin film on the elastic fabric tape may include one or more of spray-coating, screen-printing, inkjet printing, and micro plotting.

In embodiments, the geometrical pattern may be a grid.

In embodiments, another step may include generating a digital twin characterizing a MSK system of a subject using the strain distribution and strain directionality data. Yet another step may include updating the digital twin to assess changes in the MSK system of the subject by repeating one or more of the above steps.

Additional aspects of the present disclosure relate to a sensing mesh. The sensing mesh may include an elastic fabric tape conformable to skin near a region of interest on a body. The elastic fabric tape may be arranged in a geometrical pattern to form an interconnected network. The elastic fabric tape may be adherable to the skin. A nanocomposite thin film may be disposed on the elastic fabric tape. An electrode may include conductive threads.

In embodiments, the region of interest may include one or more of a bicep region, pectoral region, latissimus dorsi region, gastrocnemius region, quadricep region, ankle region, knee region, elbow region, back region, and neck region.

In embodiments, the nanocomposite thin-film may include one or more of a graphene nanosheet, carbon nanotubes, carbon black, and silver nanoparticles.

In embodiments, the conductive threads, fibers, or wires may electrically couple edges of the sensing mesh together.

In embodiments, disposing the nanocomposite thin film on the elastic fabric tape may include one or more of spray-coating, screen-printing, inkjet printing, and micro plotting.

In embodiments, the geometrical pattern may be a grid.

Additional aspects of the present disclosure relate to a method include a number of steps. One step may include interrogating a sensing mesh using an electrical impedance tomography (EIT) device. The sensing mesh may be affixed onto skin nearby a musculoskeletal (MSK) region of interest. The sensing mesh may include a graphene nanosheet (GNS) thin film sprayed on elastic fabric tape. The sensing mesh may form a geometrical pattern on the skin. Another step may include generating, in real-time, EIT conductivity maps using data measured from interrogating the sensing mesh with the EIT device. Yet another step may include generating, in real time, strain distribution and strain directionality data of the MSK region of interest using the EIT conductivity maps.

In embodiments, the MSK region of interest may include one or more of a bicep region, pectoral region, latissimus dorsi region, gastrocnemius region, quadricep region, ankle region, knee region, elbow region, back region, and neck region.

In embodiments, the sensing mesh may include conductive threads, fibers, or wires electrically coupling edges of the sensing mesh together.

In embodiments, the geometrical pattern may be a grid.

In embodiments, synthesizing the GNS thin may include uniformly dispersing GNS to form stable polyelectrolyte solutions with no phase segregation:

In embodiments, synthesizing the GNS thin film may include annealing the GNS thin film.

In embodiments, another step may include generating a digital twin characterizing a MSK system of a subject using the strain distribution and strain directionality data. Yet another step may include updating the digital twin to assess changes in the MSK system of the subject by repeating the above steps.

BRIEF DESCRIPTION OF THE DRAWINGS

The technology disclosed herein, in accordance with one or more various embodiments and referred to as Motion Tape, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

DETAILED DESCRIPTION OF THE EMBODIMENTS

Figure 1:
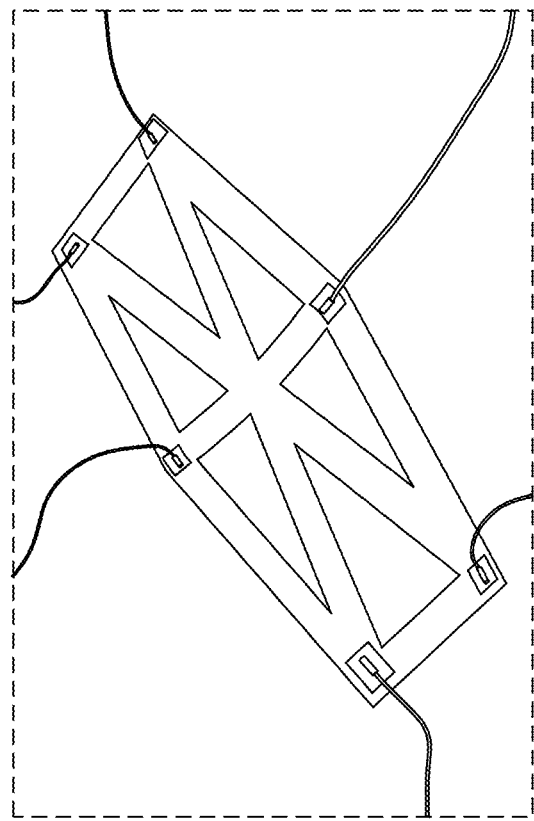
FIG. 1 is an example nanocomposite thin film sensor and network of Motion Tape forming distributed sensing, in accordance with various embodiments of the present disclosure.
Figure 1:
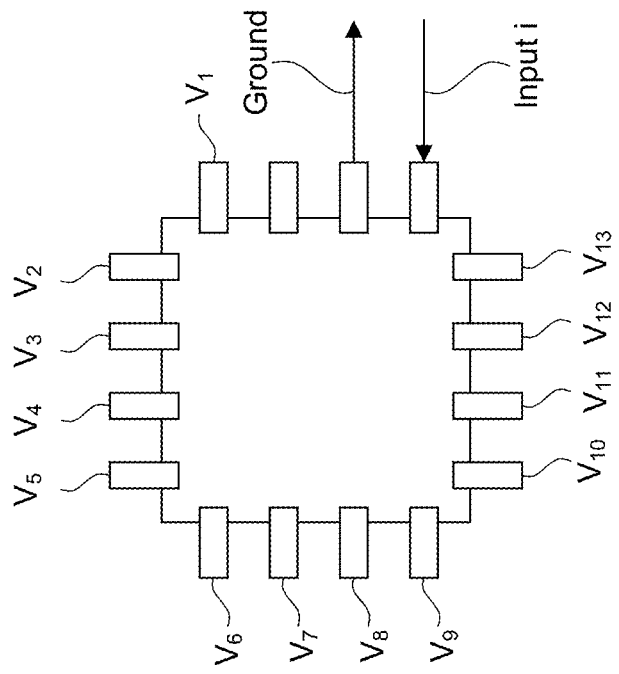
Figure 2:
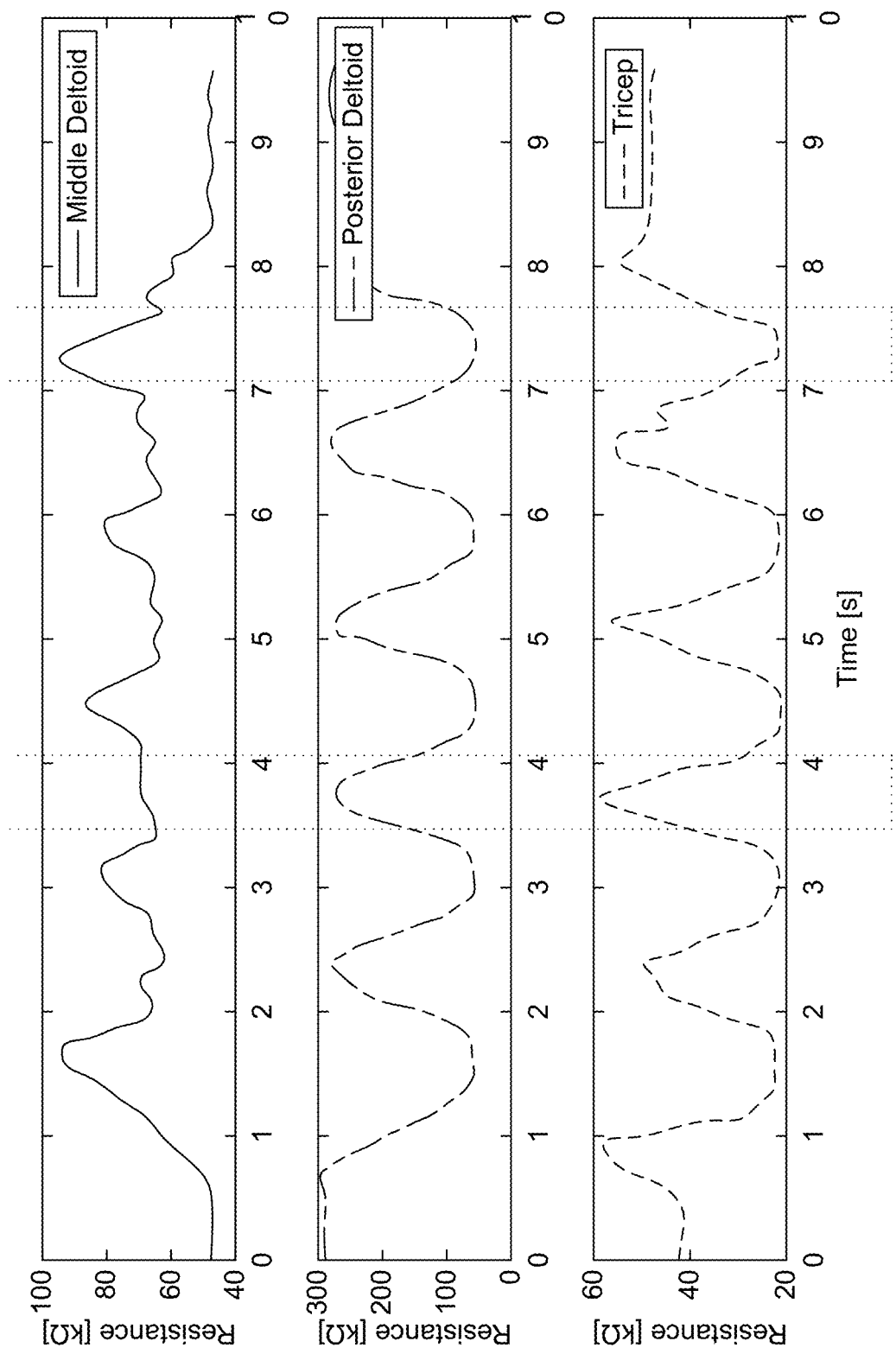
FIG. 2 illustrates data from mounting the presently disclosed technology on a body and interrogating the presently disclosed technology over time while the subject does push-ups, in accordance with various embodiments of the present disclosure.
Figure 3:
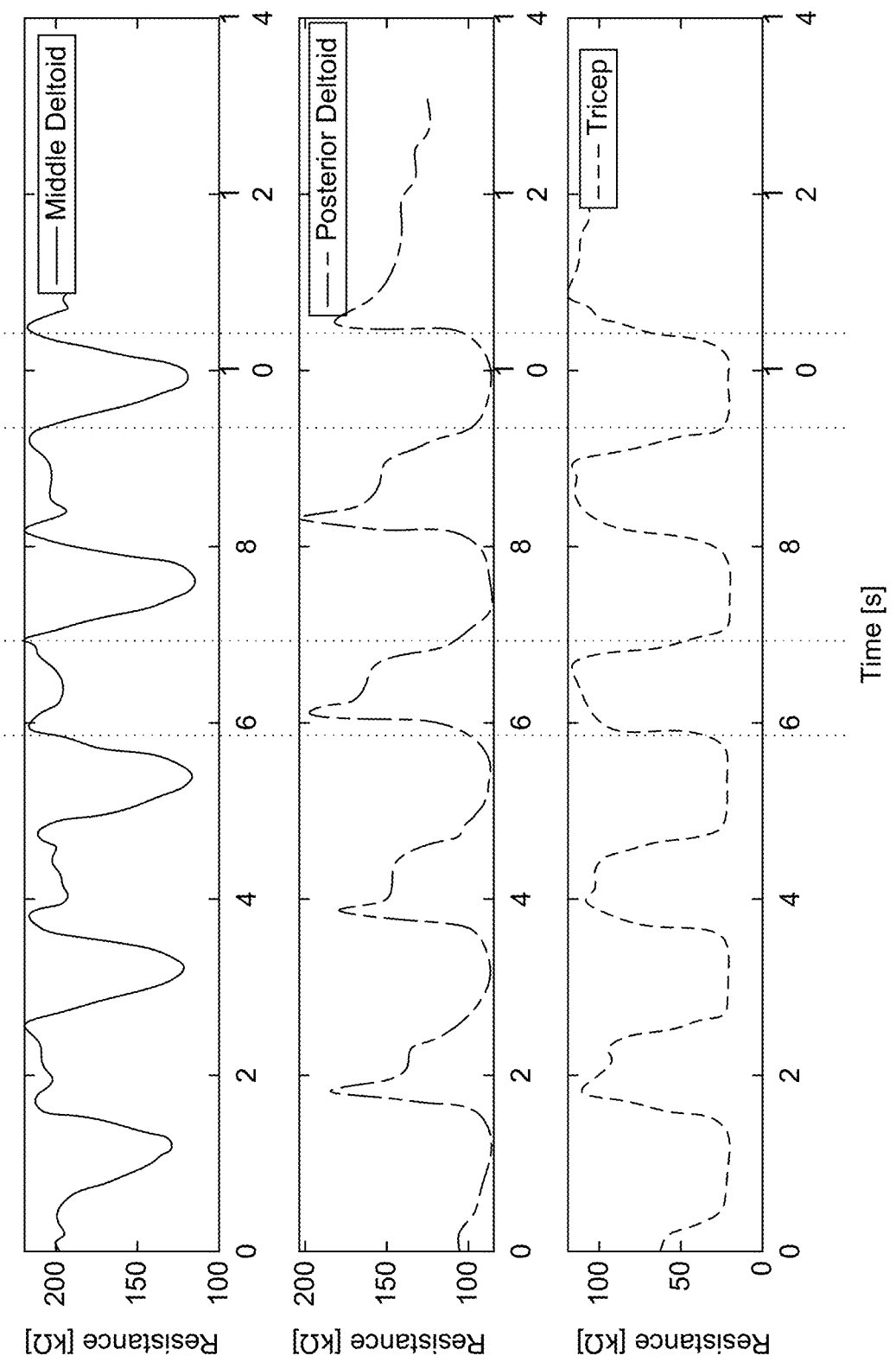
FIG. 3 illustrates data from mounting the presently disclosed technology on a body and interrogating the presently disclosed technology over time while the subject does triceps dips, in accordance with various embodiments of the present disclosure.
Figure 4:
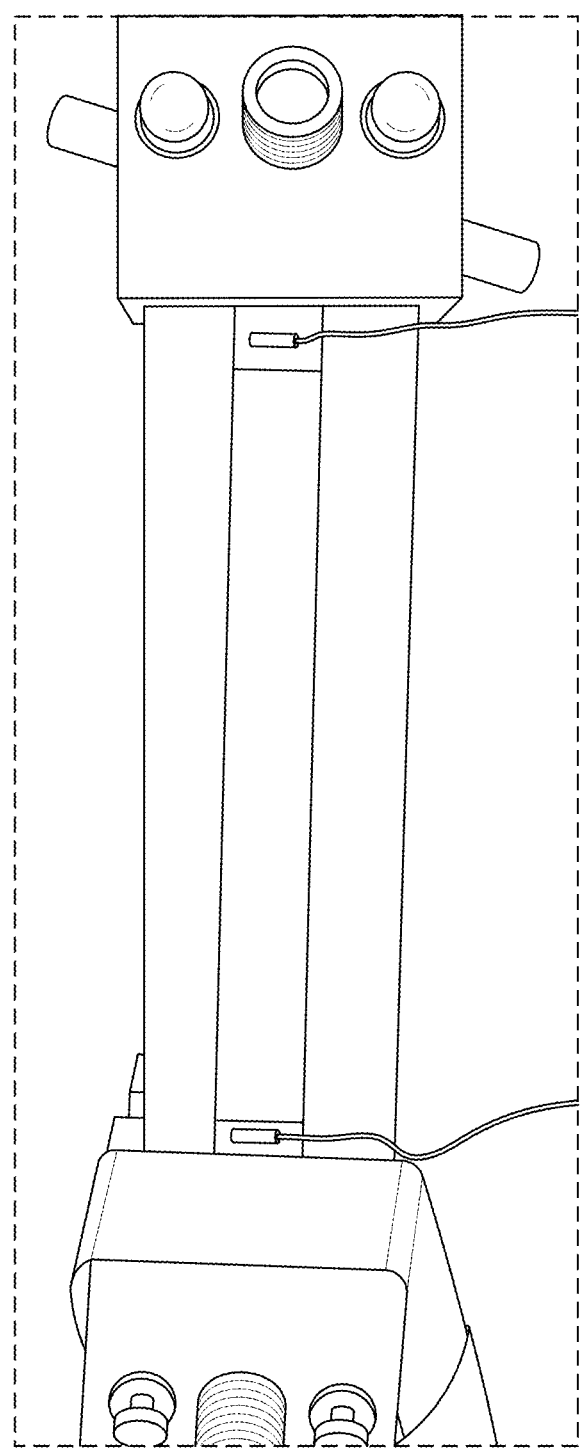
FIG. 4 illustrates testing the presently disclosed technology using a load frame, in accordance with one embodiment of the present disclosure.

Musculoskeletal (MSK) injuries are the leading cause of military disability discharge, and even minor injuries that temporarily remove the warfighter from combat, active service, and/or training will decrease operational readiness. For example, each year, about 1.6 million MSK injuries occur within the U.S. Department of Defense, where disease and non-battle-related injuries have surpassed those due to combat. The majority of such injuries are classified as inflammation or pain from overuse, which are often incurred during physical training, tactical training, and recreational activities. For male military trainees, lower-back pain and tendinitis are more predominant, whereas female trainees are frequently diagnosed with muscle strain and stress fractures. Although most MSK injuries are non-life-threatening, their high incidences adversely affect warfighter and operational readiness. The presently disclosed technology may be used in prehabilitation, where the warfighter will be able to: measure and monitor his or her health; fine-tune training and service activities to increase performance; identify early signs of micro-injuries; and modify activities accordingly to prevent MSK injuries. Currently existing technology does not provide field-deployable, unobtrusive, wearable sensors that can be used during training, as well as in forward-deployed operations, that can reliably acquire high-quality quantitative data of warfighter motions with direct insights of individual MSK health.

For example, while wearable sensors can be an ideal platform for monitoring warfighter health and the occurrence of MSK injuries during training and active service, the mainstream strategy of designing wearable sensors is to integrate commercially available sensors in a compact hardware package. In general, many commercial and research-based wearables focus on monitoring vital signs (e.g., heart rate, steps, peripheral oxygen saturation, and body temperature), which provide a global sense of physical well-being. Those focused on physical activity monitoring have integrated conventional sensors, such as force transducers, gyroscopes, accelerometers, and magnetometers, in a single package. Unfortunately, their large form factors and rigid structures often cause discomfort and is an additional device (or weight) that the warfighter may haul. Hybrid wearable sensors that miniaturize different sensor components (with some incorporating electromyography (EMG) sensing) into a single electronic chip with ultra-low power consumption have also been studied. Although they can provide a more holistic assessment of muscle movement dysfunction related to MSK injuries, these devices output measurements at the location where they are worn. Wearable sensors that can quantify MSK health in relation to lower-back pain, injuries such as in the extremities (e.g., tendinitis), and muscle strain at different bodily locations remain challenging. Overall, characterizing MSK movement, injury precursors, and the health of different parts of the moving body cannot be effectively achieved today, even if many of today's wearable transducers are worn simultaneously. While warfighters are used above, this is merely for exemplary purposes and it should be understood that the presently disclosed technology can be applied to any subject.

Flexible sensors can be worn at locations where traditional wearable devices would otherwise be unsuitable simply due to their limited stretch-ability. For example, fabric-based sensors, such as a wearable t-shirt with an integrated motherboard to monitor vitals and soft elastomeric sensors embedded in garment to measure hip, knee, and ankle kinematics, have been investigated. More recently, a silicone elastomer-based stretchable capacitive sensor has been proposed for strain and pressure sensing, which can be integrated in gloves to monitor finger motion, pressure, and tensile forces. However, most of these latest works are still discrete transducers that measure data where they are instrumented, and full-field physical monitoring still use many sensors and the associated cabling and data acquisition components. These challenges are in addition to the fact that fabric-based sensors may not be best-suited for every location of the body.

In short, commercial- and research-based wearable sensors still suffer from several limitations that, in turn, result in inaccurate data and provide a limited view of warfighter physiological performance. Current technology gaps that are continued to be researched and alternative solutions are summarized as follows:

Sensor form factor to be unobtrusive and cannot affect warfighter function/performance.

Different types of wearable sensor substrates that can conform to various body parts for effective measurements.

High sensitivity and accuracy for identifying MSK injury precursors (e.g., slight changes in movements and motion patterns).

Sensor measurements to be independent of ambient effects (e.g., temperature).

Distributed or full-field sensing using the least possible number of measurements (electrodes) not only minimize sensor form factor but also to characterize muscular/bodily movements at distributed locations.

Detailed measurements about the extent of how muscles engage during functional movements.

Additional issues for piezoresistive sensing skins coupled with the EIT algorithm persist. First, a separate analytical inverse piezoresistive numerical model may be used to extract strain directionality from the reconstructed EIT conductivity maps. In some embodiments, comparatively low strain sensitivities of the CNT thin films make it challenging for detecting small changes in strain.

The Navy and warfighters do not have suitable wearable sensors that can monitor their MSK health nor the capability to tailor training (or rehabilitation) activities. Each warfighter is expected and may ultimately perform the same functional duties, but improper training and form can result in higher risks and the earlier onset of severe MSK injuries. The presently disclosed technology includes a multifunctional wearable sensing platform for real-time, distributed, physiological monitoring of performance.

Wearable sensors for human motion and physiological monitoring has attracted substantial attention in recent years, especially for applications such as sports performance, virtual/augmented reality, gesture recognition, and healthcare. Most commercial wearable sensor platforms today are based on physical electronic devices such as watches, bracelets, and necklaces, which may have individuals make a conscious effort to incorporate such technologies in their daily life. In contrast, wearable sensors in the form of patches or thin films can be worn and be forgotten. The presently disclosed technology integrates sensing functionalities with kinesiology tape (K-Tape), which, on its own, is already widely used in athletics and rehabilitation. This is achieved by directly spray-coating and depositing graphene-based thin film strain sensors onto K-Tape. Upon fabricating Motion Tape specimens, their strain sensing properties were characterized. Then, the sensor may be adhered onto a subject's arm for validating its ability to capture and quantify repetitive motions. The results, discussed herein, confirmed their stable and repeatable strain sensing performance.

Moreover, the "Internet-of-Things" has revolutionized how individuals perceive and interact with the world on almost all facets of life. With rising global health issues as well as greater desires for improving personal wellness and health, wearable sensors have drawn immense interests due to their ability to monitor an individual continuously. For instance, many wearable sensors employ conventional accelerometers and gyroscopes, which are packaged in the form of a watch, bracelet, or necklace, as means to monitor human motion. Although many commercial devices are available and are popular, these wearables may have individuals make a conscious effort to incorporate such technologies in their daily life. These wearables are often too bulky, which remains to be the major limitation for acceptance and use by certain population groups such as athletes, the military, and the elderly. The presently disclosed technology discloses lightweight, flexible, and low-profile sensors that can be mounted on an individual's skin and be forgotten by the user while continuously recording human performance-related parameters of interest. Such wearable sensors could find broad uses cases ranging from human performance assessment to athletic training to sports coaching to personal activity monitoring to gesture recognition to rehabilitation to general health and well-being assessment.

Distributed strain monitoring may use a dense array of gages installed on the structure. Despite their accuracy and high resolution, each strain gage can only measure strain at its instrumented location (i.e., it is a point sensor). More recently, distributed strain sensing and damage detection may be achieved by coupling piezoresistive thin films with an electrical impedance tomography (EIT) measurement technique and algorithm. While strain distributions could be characterized, this approach may be unable to extract strain directionalities from the reconstructed EIT conductivity maps. The sensing mesh concept introduced in the presently disclosed technology may address this limitation. In some embodiments, a graphene-based thin film of high strain sensitivity may be deposited onto a patterned substrate to form the sensing mesh. Each strut of the sensing mesh may be designed to be of high aspect ratio so as to form an interconnected network of distributed uniaxial linear strain sensors. EIT may be implemented to reconstruct the conductivity changes of the struts in the mesh. The estimated conductivity changes were then used to calculate the induced strains in each strut.

The presently disclosed technology may be used for monitoring and characterizing physical activity (during daily activities, training, and in-service). The presently disclosed technology may be used as a technology platform for other functionalities, such as biosensors, flexible electronics, energy harvesting, and energy storage to be seamlessly integrated together. These sensors and methods can be used during training or deployment for: (1) identifying micro-injuries or injury precursors; (2) augmenting activities that enhance and sustain performance; (3) assessing capabilities among different groups (e.g., male versus female); (4) facilitating active rehabilitation of the wounded and their faster return to service; and (5) maintaining overall health. Overtime, the wearable sensors and subsequent modified activities will decrease MSK injury rate, personnel downtime, and discharge, thereby increasing operational readiness of users. Furthermore, the wearable sensing platform will provide data streams of performance and health that can potentially transform how to assess, train, and manage active personnel.

In embodiments, flexible fabric- and tattoo-based nanocomposite wearable sensors may be used. The presently disclosed technology may include real-time distributed (i.e., spatial) sensing measurement strategies and algorithms. The presently disclosed technology may include field-deployable and portable data acquisition solutions for interfacing with the wearable sensors. The presently disclosed technology may optimize sensor performance through validation of motion monitoring in controlled laboratory and simulated operational conditions.

Due to the human body undergoing complex motions at different regions (e.g., torso versus extremities), the presently disclosed technology includes skin-mounted wearable sensors that can be worn at various locations while acquiring high quality movement data. In one example, a sensor platform may include one of tattoo-like thin films and self-adhesive fabric-patch-based wearable sensors. The different wearable substrates may rely on appropriate nanocomposite thin film sensor fabrication approaches (as well as nanocomposite formulations to attain high performance) that integrate the sensing elements. In some embodiments, geometrical patterning may be employed to enhance sensor performance attributes while minimizing ambient (temperature) effects that would otherwise contaminate the sensing streams acquired. Depending on the locations-of-interest and the types of motion to be quantified, different patterning of the wearable sensors and unique measurement strategies may be implemented to characterize full-field bodily or muscular motion. In one example, the presently disclosed technology may acquire as few measurements as possible while using tomographic methods and the patterned nanocomposite to realize spatially distributed sensors. In embodiments, a miniature and portable wireless data acquisition node may interface with the wearable sensors to facilitate real-time measurements in variable environments.

Disclosed are methods, designs, materials, sensors, devices and systems that pertain to thin film strain sensors integrated with self-adhesive elastic fabric tape. Embodiments of the presently disclosed technology can be affixed onto different parts of the body to form a mesh/grid-like network, commonly used for physical therapy, with the ability to measure strains along the elastic fabric element. The design and use of a mesh/grid-like network of Motion Tape allow sensing of distributed strains along the body/muscles (for quantifying muscular activity, movements, and physical motion). With the electrical impedance tomography (EIT) method, a few voltage measurements (taken along the boundaries of the entire mesh) are used to back-calculate the entire distribution of strain in the Motion Tape mesh, generating a strain map or image along the entire body. The presently disclosed technology has broad application potential for physical therapy, athlete/warfighter assessment, healthcare monitoring, wearable products and the like.

In one example, human physical activity and movements may be monitored by directly measuring strains on the skin. However, conventional strain gages are not suitable for this due to their rigid nature. Instead, piezoresistive nanocomposite thin films whose electrical resistance changes when strained are promising for designing low-profile, conformable, wearable sensors. For example, such strain sensors have been fabricated using dry-spun carbon nanotube fibers embedded in Ecoflex, which is a highly flexible elastomer directly printed graphene ink onto commercial medical tape to realize a wearable strain sensor. It may be shown that the highly flexible printed graphene sensor could be used for monitoring physical motion, eye blinks, and pulse.

In some embodiments, a graphene-based wearable strain sensor may be designed using commercial kinesiology tape as the sensor substrate. K-Tape is a highly elastic cotton tape used in sports medicine and rehabilitation, where the tape and acrylic adhesive backing are designed to pull the skin surface in a way that could facilitate or inhibit musculoskeletal motions. In embodiments, spray-coating graphene nanosheet (GNS) dispersions may be sprayed onto masked K-Tape strips. Then, their strain sensing properties were characterized through electromechanical tests conducted using a load frame. In some embodiments, the sensor may be adhered onto a subject's arm and validated for capturing repeated muscular contraction and extension motions.

Aim #1—Wearable Nanocomposite Sensor Design

The presently disclosed technology includes high-performance, low-profile, and conformable nanocomposite wearable sensors for human motion monitoring. This wearable sensors may include a self-adhesive, fabric-like patches such as commercial kinesthesiology tape (K-Tape) and ultra-thin, ultra-flexible medical tape. Engineering these fabric-based materials to measure muscle strains may provide a wearable sensing platform ideally suited for capturing motion across large, spatially distributed regions of the body. The ultra-thin medical tape can conform to nonuniform surfaces and be engineered with nanocomposite sensing elements for capturing intricate and sensitive movements.

With respect to the wearable sensors, the strain sensing properties of graphene nanosheet (GNS) polymer nanocomposite thin films may be used, depending, in part, on the type of substrate used for deposition. In embodiments, the flexible, self-adhesive, fabric-based sensors may be fabricated by depositing GNS-polymer thin films onto commercial K-Tape or other like material. In addition, an ultra-thin wearable strain sensor may be fabricated by depositing nanocomposites onto tattoo-like medical tape. In some embodiments, patterning of the thin film sensing element to form different topological designs may be a fabrication technique.

The GNS-based thin films may include electrical properties that are sensitive to applied strains, and which can then be integrated with low-profile, flexible substrates using appropriate scalable fabrication techniques. In some embodiments, the GNS may be uniformly dispersed in polymer-based solutions, while the selection of the dispersing agent may depend on the substrate and a suitable fabrication method for reliably forming the nanocomposite thin films. For example, prior to film fabrication, GNS may be uniformly dispersed to form stable polyelectrolyte solutions with no phase segregation. The dispersed GNS solution or ink formulation may consider the polyelectrolyte specie(s) employed, their chemical properties, solution viscosity, and hydrophobicity, to provide an exemplary list. It should be appreciated that other aqueous solutions may be used, such as those based on poly(vinyl alcohol) (PVA), ethyl cellulose (EC), and poly(sodium-4-styrenesulfonate) (PSS), among others, which have been shown to effectively disperse GNS. The viscosity of the GNS ink may be adjusted so that films can be fabricated by spray-coating, screen-printing, and inkjet printing.

GNS-polymer nanocomposite thin films may be fabricated using one of methodologies disclosed herein (e.g., spray-coating, screen-printing, and inkjet printing) and of varying polymer matrices (e.g., PVA, EC, and PSS), viscosities, and GNS concentrations. In embodiments, films may be fabricated on polyethylene terephthalate (PET) sheets. The physical properties and film morphology may be characterized using electron and optical microscopy, for assessing GNS dispersion and its integration in the polymer matrix. The ability to control the spatial resolution of films fabricated may also be investigated by depositing films of different widths and assessing their physical features using optical imaging. A set of film formulations may be identified and used for fabricating rectangular thin films for electromechanical characterization. Strain sensing properties, such as their strain sensitivity, resolution, accuracy, root-mean-square noise floor, linearity, and hysteresis, may be characterized and compared.

Adhesive fabric-based sensors may be fabricated using commercial K-Tape so that they can be applied (on the skin) over major muscle groups for human motion characterization. The GNS ink formulations and their corresponding fabrication method may be employed. In embodiments, for spray-coating and screen-printing, K-Tape substrates may be masked to leave bare regions for film deposition (e.g., rectangular regions). In some embodiments, inkjet printing may not use masking, and computer aided design (CAD) software may be used to directly reproduce desired film geometries on K-Tape. In some embodiments, microscopy may be used to assess the physical characteristics of the as-deposited films to ensure that a dense GNS-polymer matrix is formed. Mild thermal annealing using a vacuum oven can be performed to further densify the films and ensure better bonding with K-Tape. It should be mentioned that the adhesive side of the K-Tape may also be examined to ensure that the deposited GNS solution does not bleed into the substrate and reduce the overall spatial resolution of films deposited. If this cannot be prevented, the GNS sensing elements may be deposited onto stretchable fabric transfers and then ironed onto the K-Tape substrates to form the Motion Tape sensors. Two-point probe electrodes may be created using conductive threads and colloidal silver paste. In embodiments, the K-Tape specimens may be (1) directly mounted in a load frame and (2) also affixed onto stretchable polymer substrates for electromechanical characterization. Strain sensing properties, such as their strain sensitivity, resolution, accuracy, noise floor, linearity, and hysteresis, as well as load rate effects, may be characterized and compared for design optimization.

Sensing movements and strains at highly nonuniform and localized bodily surfaces may be achieved by integrating nanocomposites with tattoo-like medical tape. Because of the ultra-thin nature of medical tape and the difficulty of performing masking, inkjet printing may be suitable for nanocomposite deposition. The appropriate GNS ink formulation may be loaded into the nanocomposite printer or micro-plotter, and different patterns of films may be deposited onto the substrates. In some embodiments, the medical tape substrate may remain flat so that it does not contact the printer head. Optimization of printing parameters may be performed to ensure that appropriate amounts of GNS ink are dispensed with respect to the printer head speed so that high-resolution geometrical film features can be produced. Upon film fabrication, two-point probe electrodes may also be established using conductive threads and silver paste. In some embodiments, conductive fibers and wires may be used, though it should be appreciated that other conductive material may be used. These smart tattoos may be affixed onto stretchable polymer substrates and mounted in a load frame for tensile cyclic electromechanical characterization.

Additionally, electronic textiles (e-textiles) that incorporate conductive materials in fabric for direct sensing (e.g., surface electro-myography (sEMG)) and actuation (e.g., functional electrical stimulation) have been developed and used. While sEMG data can inform about muscle engagement, they are susceptible to movement artifacts and greater measurement noise due to surface electrode contact effects. The presently disclosed technology is directly adhered onto skin and is not subjected to movement artifacts. In addition, the presently disclosed technology is capable of measuring the degree of muscular engagement by measuring the corresponding changes of strain of the skin in its vicinity. Subjects performed bicep curls with different weights to test this hypothesis. The responses from the presently disclosed technology collected from four standing biceps curls performed using different weights (i.e., 5, 10, 25, and 30 lb) but all by the same individual were obtained. Although all the biceps curls were conducted with the same range-of-motion, the results show that the presently disclosed technology was able to measure greater electrical resistance changes when heavier weights were lifted. The increase in peak resistance was consistent, with the 5 lb biceps curl motion resulting in the lowest resistance change and the 30 lb movement responding with the largest resistance change. These results are promising in that the presently disclosed technology can not only be used for monitoring skin-strains and joint rotation angles but also for assessing muscular engagement of a major muscle group.

Different thin film topological designs or geometrical patterns may be investigated to enhance sensitivity while minimizing the effects of temperature on sensor outputs. The hypothesis is that uniaxial-tension-induced localized stresses and strains in the nanocomposite could dramatically increase bulk material resistance, which in turn may increase strain sensitivity. This hypothesis may be tested by designing films with different degrees of stress-concentrating features. Both experimental and numerical characterization of thin film strain sensing responses were conducted. First, to validate that the topological designs could effectively concentrate or release tension-induced stresses in the films, finite element (FE) modeling using the Solid Mechanics Module of COMSOL Multiphysics may be performed. The AutoCAD-based topological designs may be imported to COMSOL to build the model geometry, and material properties may be defined based on substrate and film properties (as identified previously). Mechanical strain may be applied, and the Electrical Currents Module may be coupled with the mechanical simulations in COMSOL to estimate the electromechanical response of the patterned films. In some embodiments, based on the numerical simulation results, the GNS-based thin film topologies may be reproduced on ultra-thin medical tape using inkjet printing. Electrodes may be formed at opposite ends of the film, similar to the FE model. The wearable sensors may be mounted onto stretchable polymer substrates and loaded in monotonic uniaxial tension, while their electrical properties are recorded. Their stress-strain characteristics may be used to refine the FE models, and the strain sensing results may also be compared with simulations for verification purposes. A control sample set may also be conducted using non-patterned or rectangular films. It is expected that topologies such as the Hierarchical Dog Bone may yield the highest strain sensitivity. Finally, the sensitivity of these different topologies to different temperatures may also be studied by FE modeling and experimental testing. The grid-like films that resemble networks of vertical and horizontal film elements may exhibit different temperature-induced electrical resistance changes depending on the topologies employed. The experimentally calibrated numerical models may be utilized to design topologies that reduce thermal effects while maximizing strain sensitivity. Smart tattoos with patterned sensing elements may be fabricated and subjected to load frame electromechanical tests.

Figure 8:
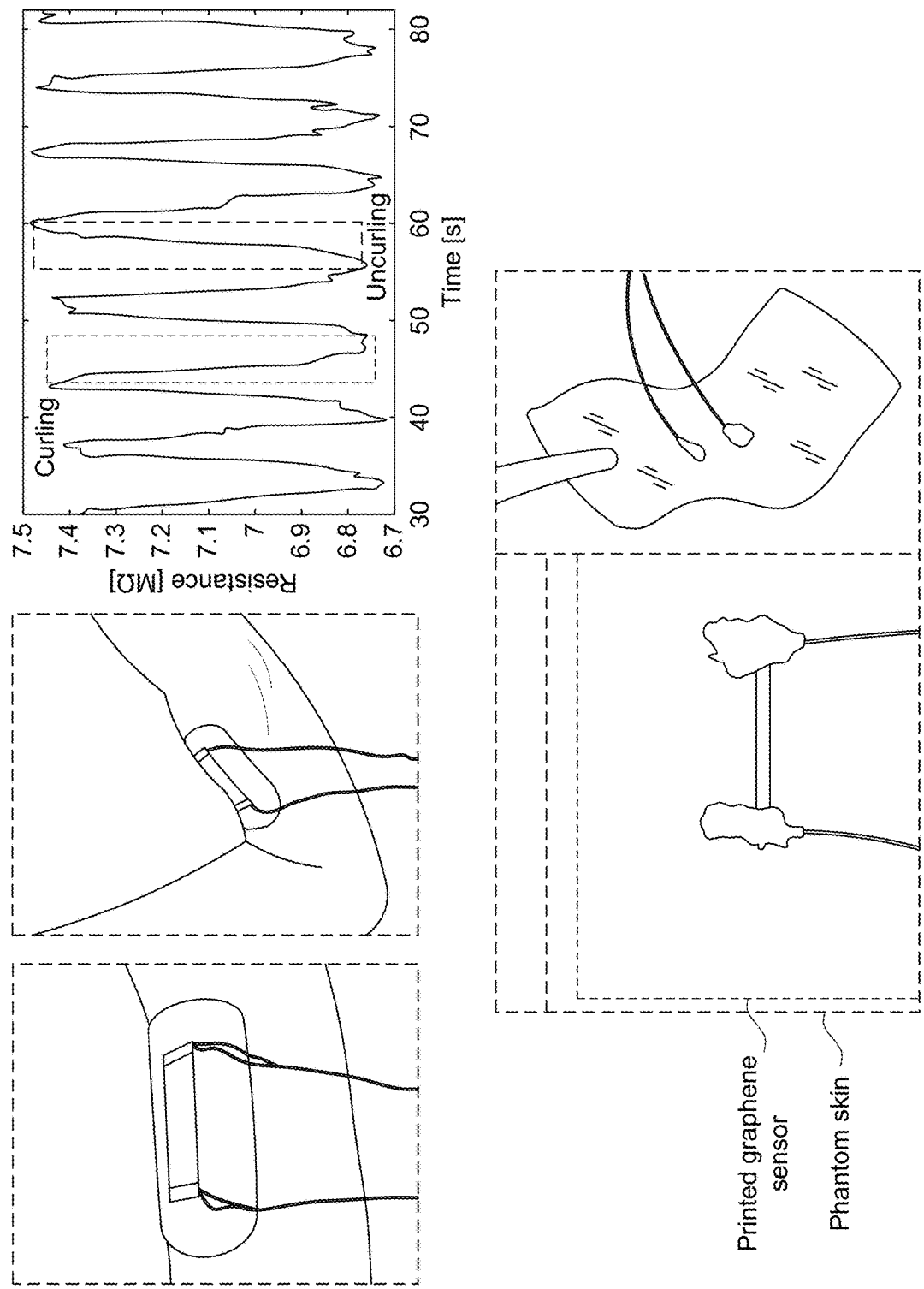
FIG. 8 illustrates example embodiments validated through human movement testing on a bicep, in accordance with one embodiment of the present disclosure.
Figure 9:
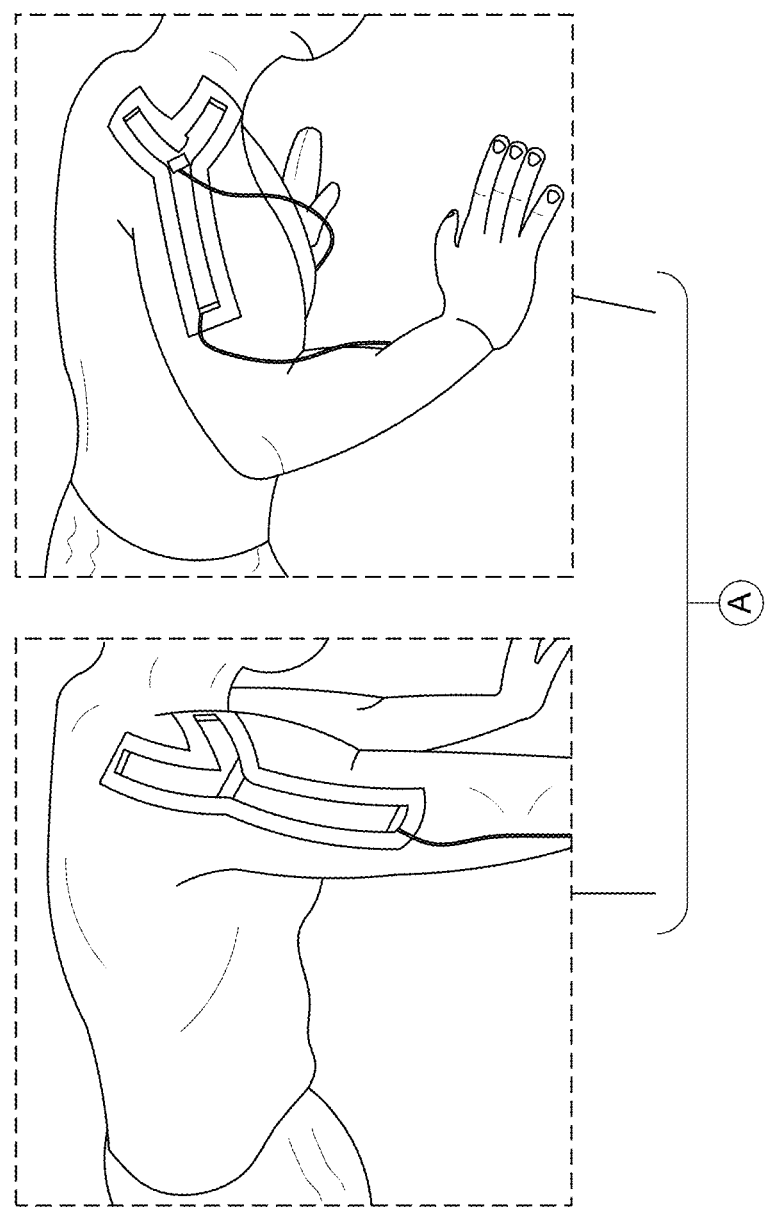
FIG. 9 illustrates example embodiments validated through human movement testing on a shoulder, in accordance with one embodiment of the present disclosure.
Figure 9:
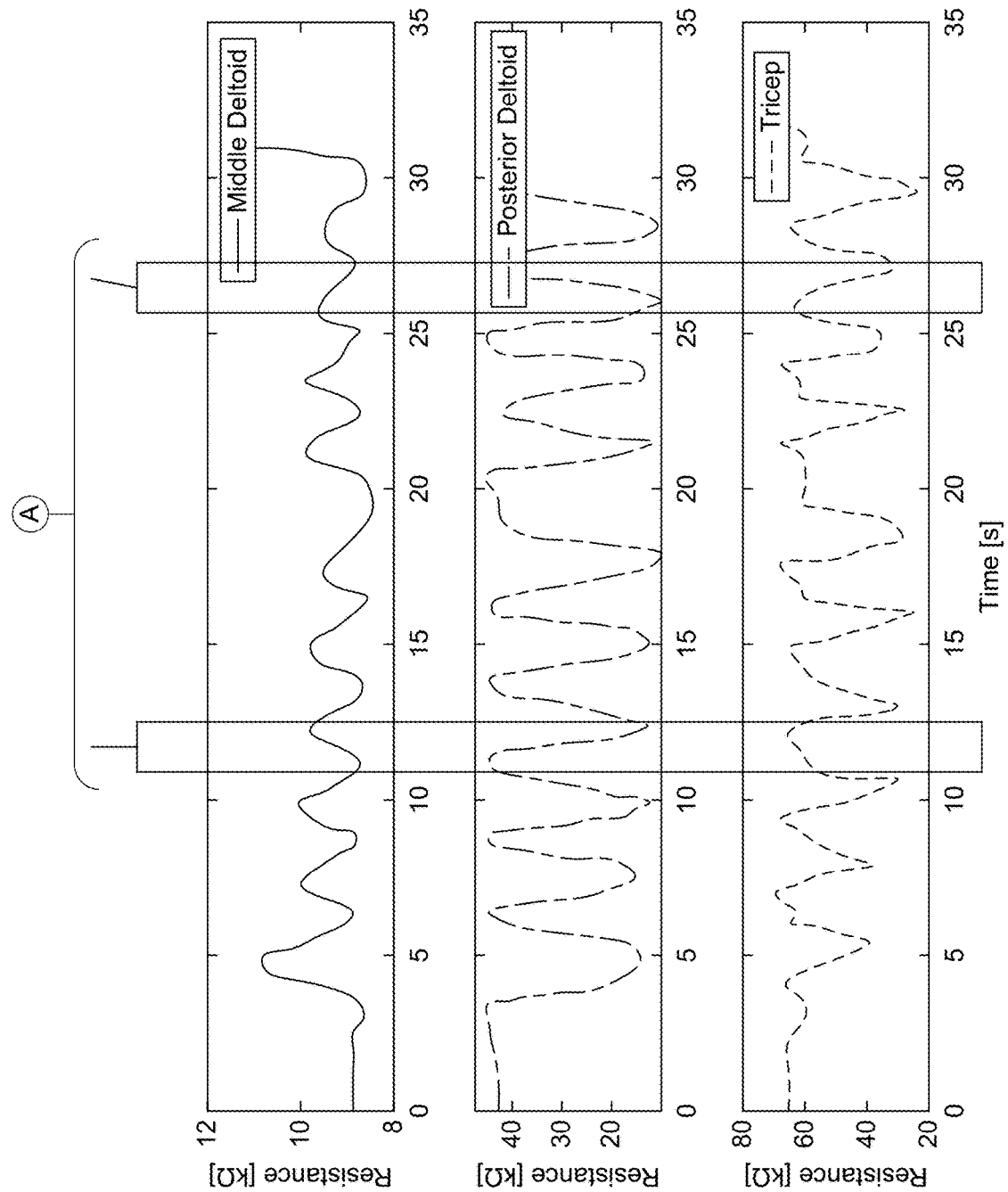
Figure 10:
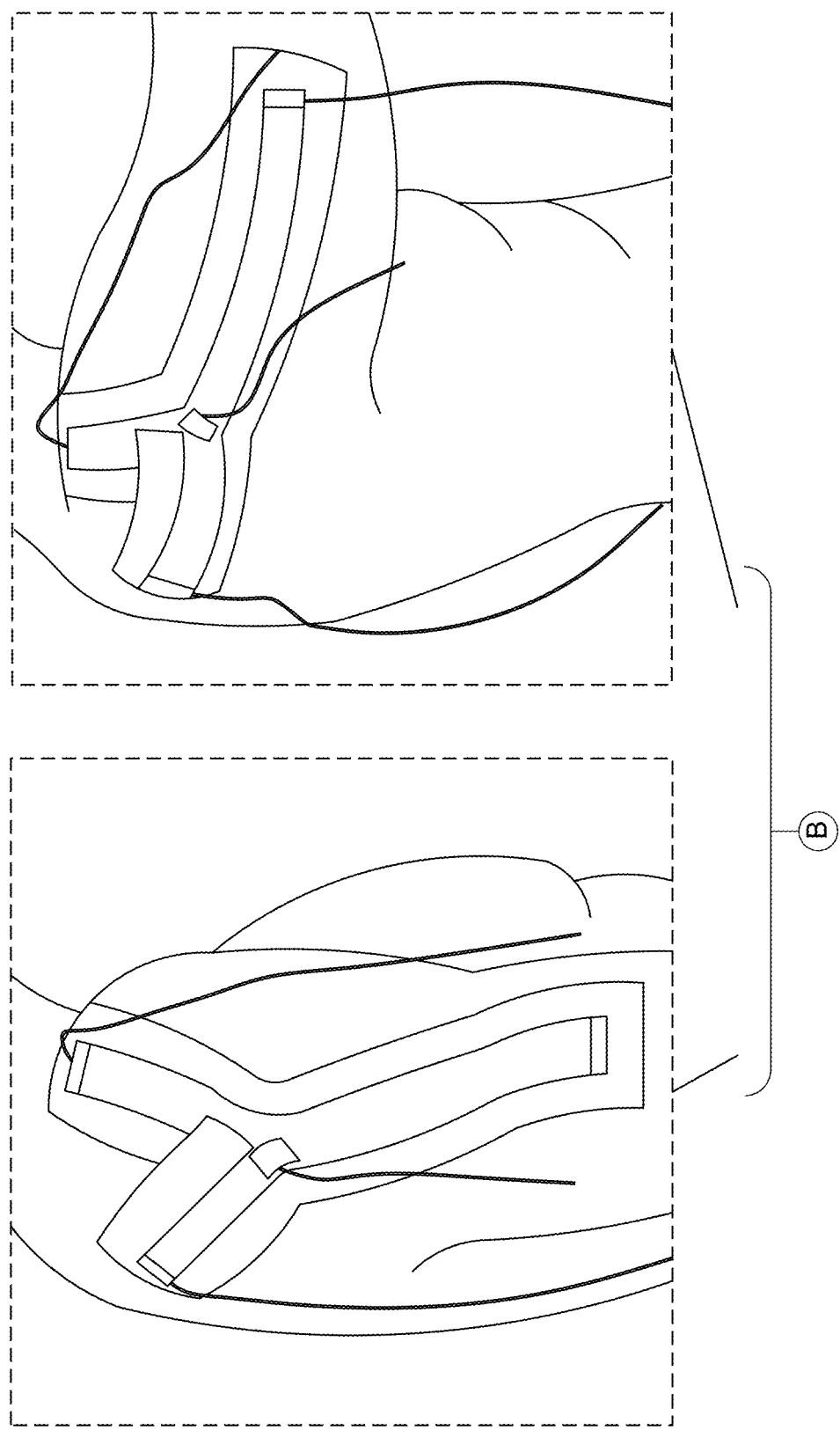
FIG. 10 illustrates example embodiments validated through human movement testing on a shoulder, in accordance with one embodiment of the present disclosure.
Figure 10:
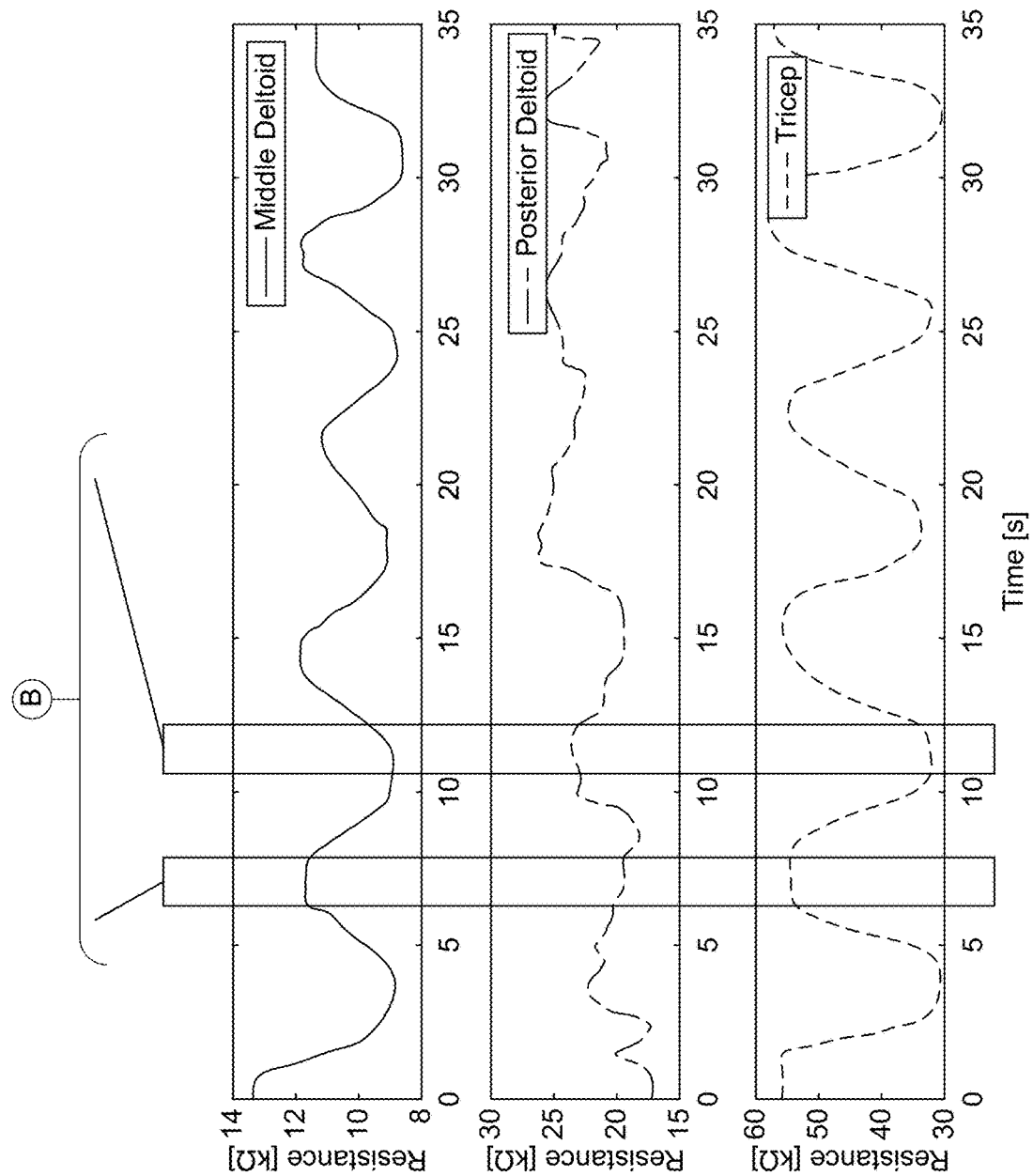
Figure 11:
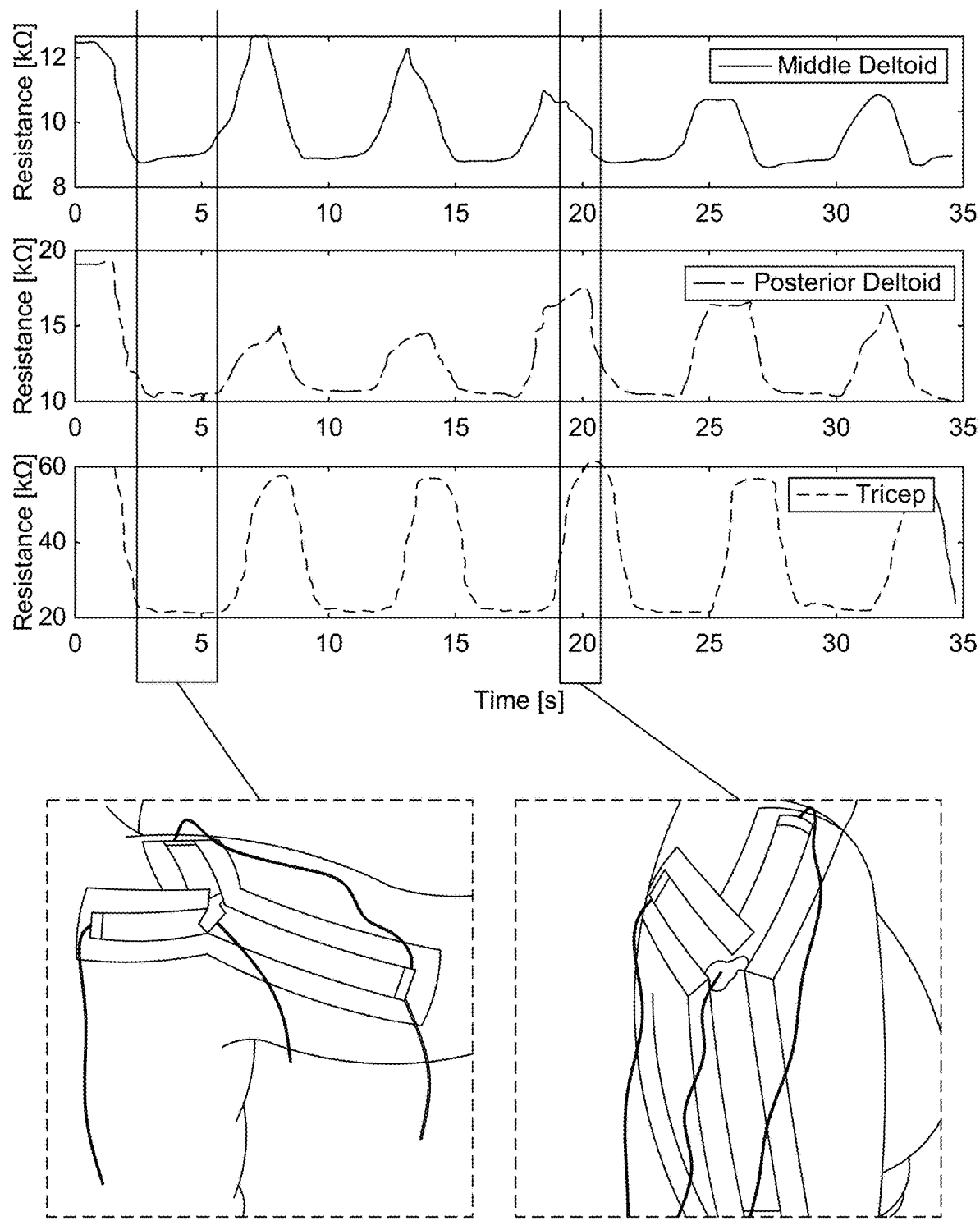
FIG. 11 illustrates example embodiments validated through human movement testing on a shoulder, in accordance with one embodiment of the present disclosure.
Figure 12:
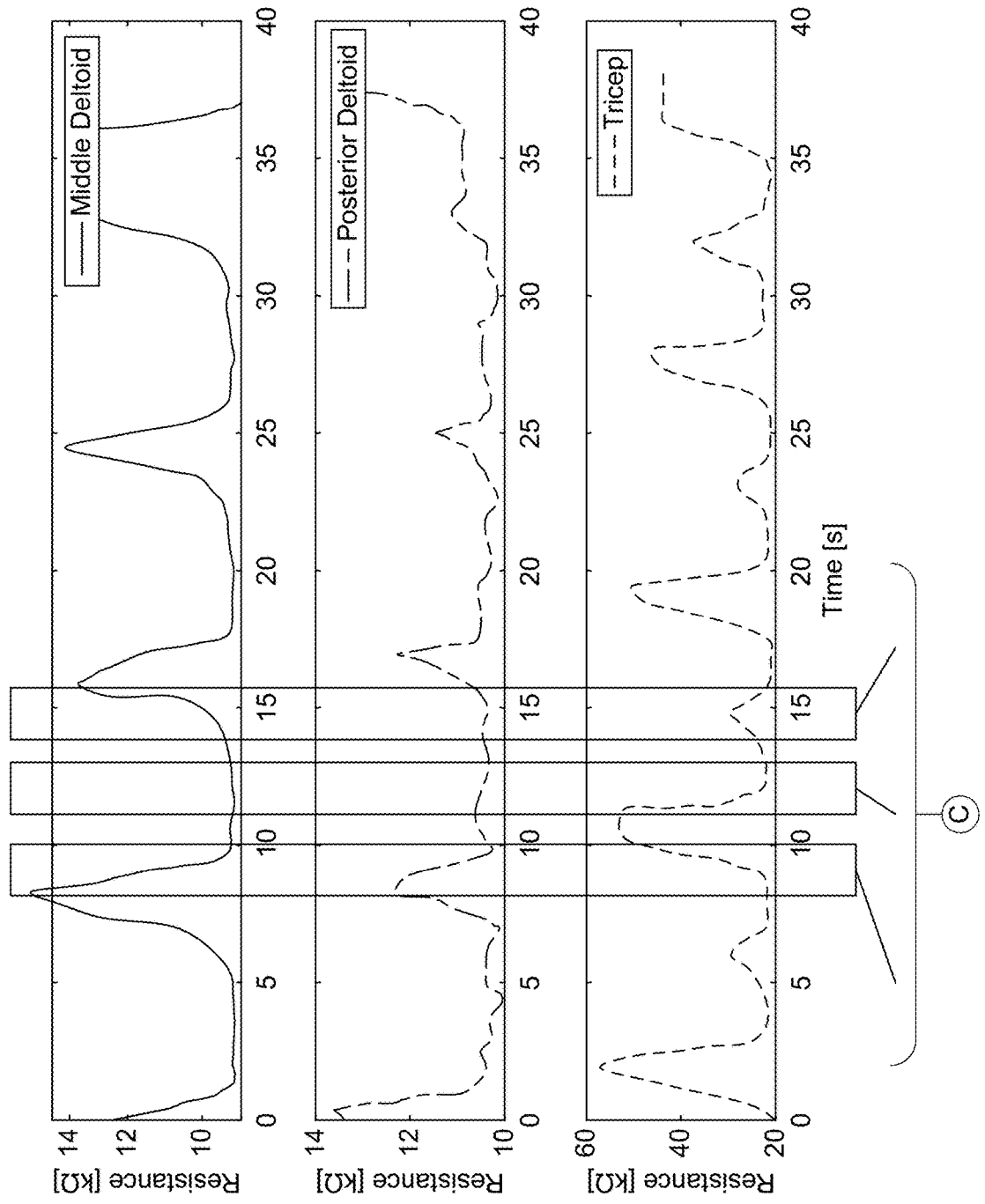
FIG. 12 illustrates example embodiments validated through human movement testing on a shoulder, in accordance with one embodiment of the present disclosure.
Figure 12:
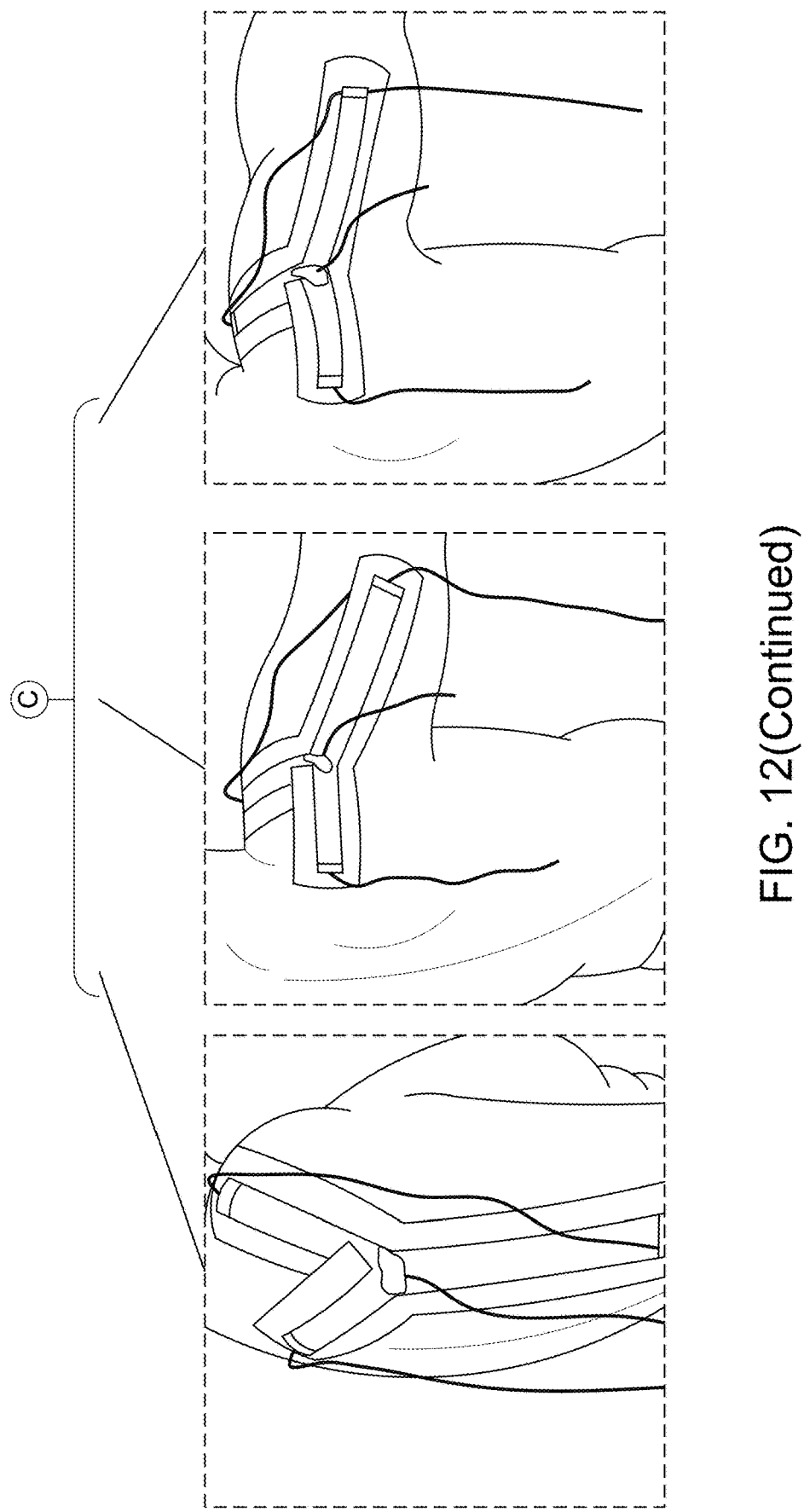
Figure 13:
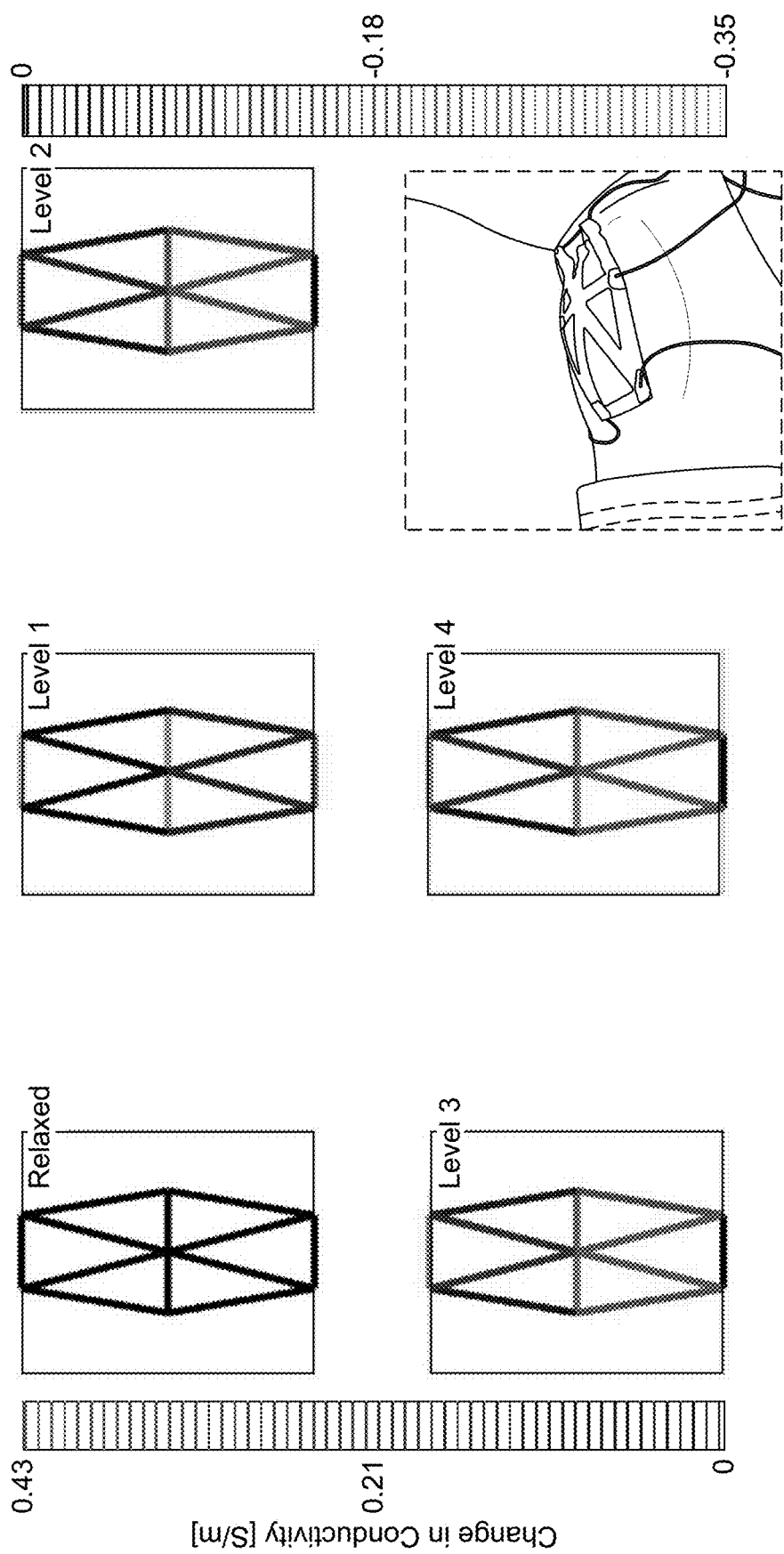
FIG. 13 illustrates example distributed strain measurements of a bicep, in accordance with one embodiment of the present disclosure.

Motion Tape and smart tattoo wearable sensors were fabricated by spray-coating and micro-plotting, respectively. FIG. 8 shows a carbon nanotube thin film strain sensor deposited onto commercial K-tape, and electrodes were formed using conductive threads and silver paste. Motion Tape may be also affixed onto a subject's upper arm, and the results in FIG. 8 confirm that electrical resistance changes correlated well with flexing and relaxing of the bicep muscle group. Using a micro-plotter, GNS nanocomposite wearable sensors were also successfully deposited onto medical tape (FIG. 8) and were characterized by gage factors (or strain sensitivities) of up to 21 when strained up to 10%.

Figure 6:
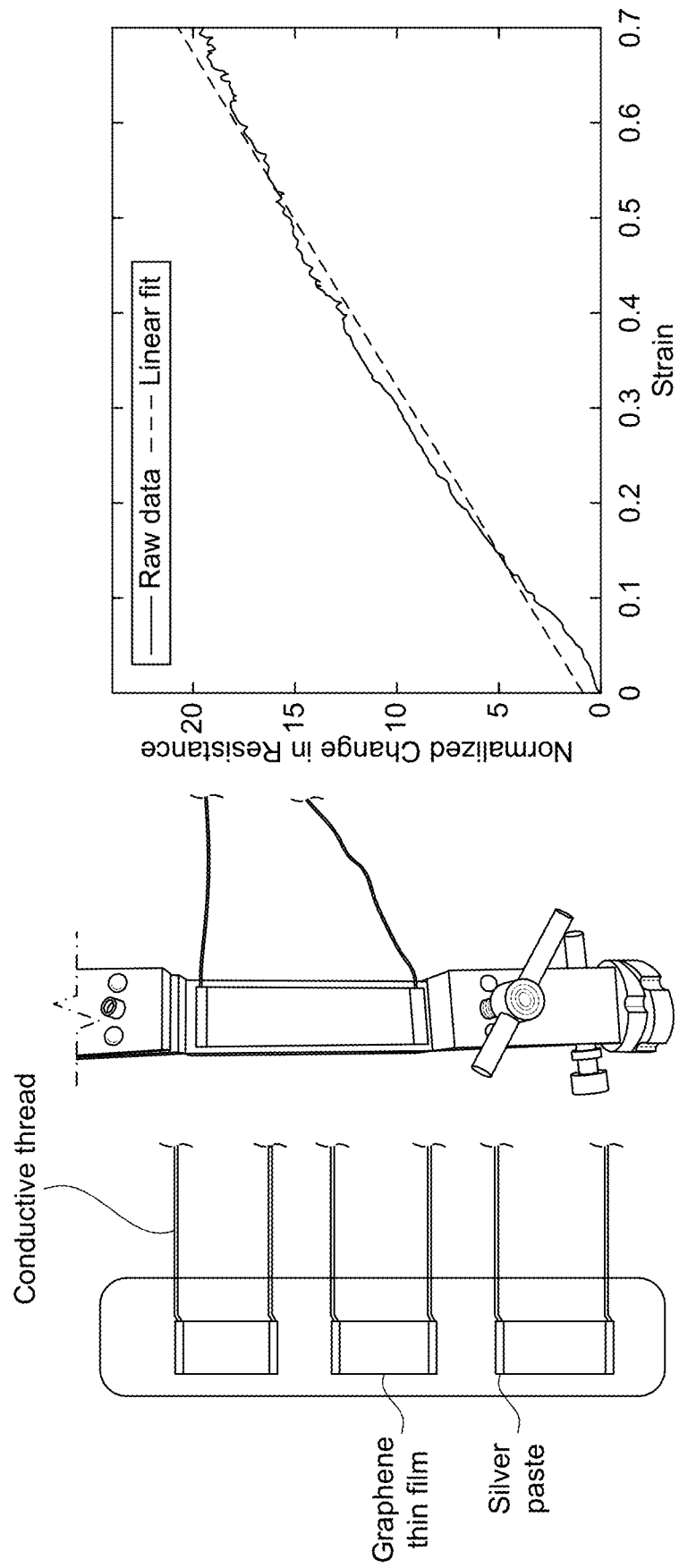
FIG. 6 illustrates example thin films subject to uniaxial tensile loading, in accordance with one embodiment of the present disclosure. For example, (a) A Motion Tape with three discrete graphene nanosheet (GNS)-based strain sensing elements is shown. (b) The normalized change in resistance of a representative Motion Tape sensor subjected to uniaxial tensile strains is plotted with respect to the applied strains to show its near-linear performance.
Figure 7:
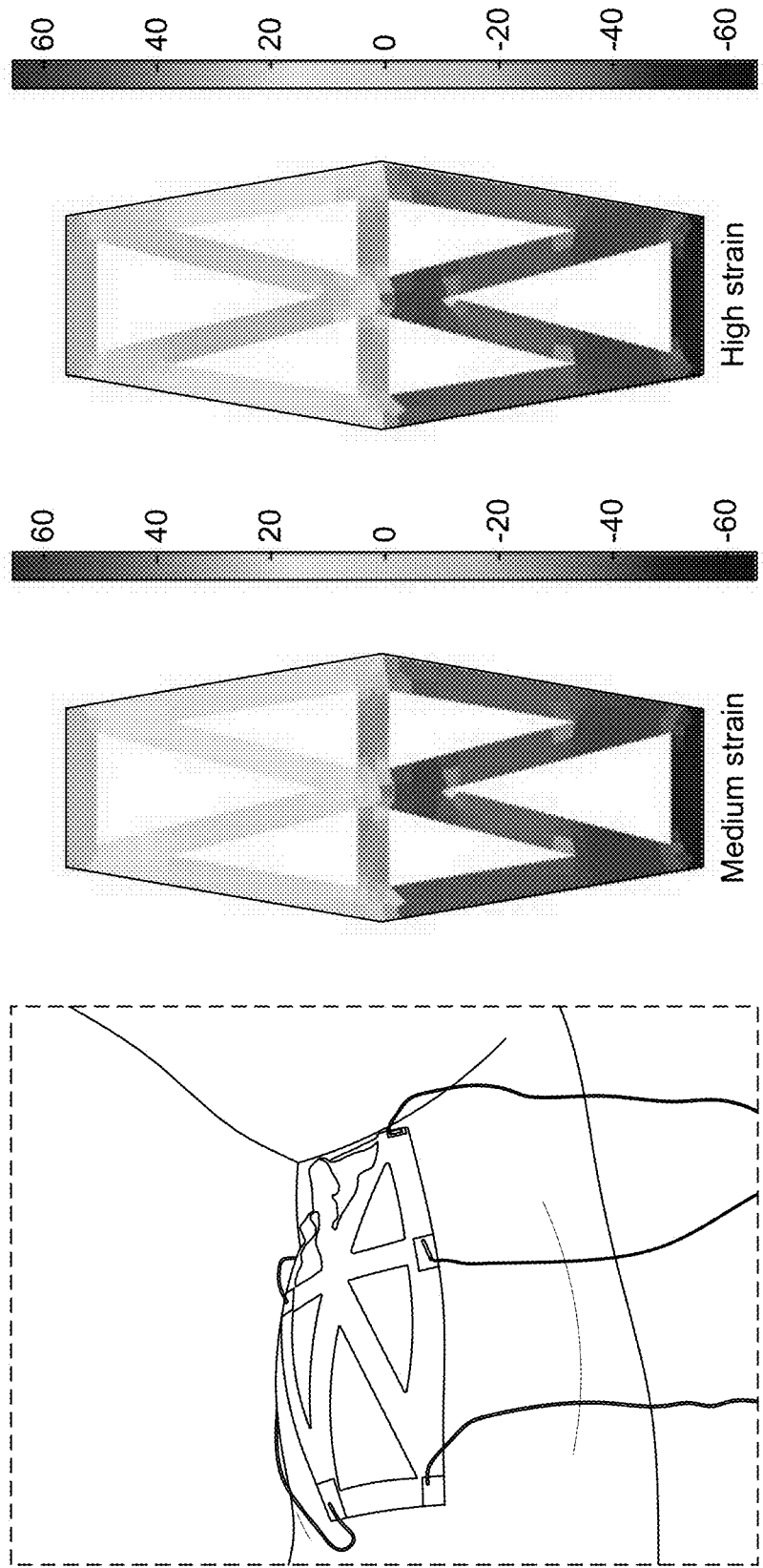
FIG. 7 illustrates distributed muscle strain monitoring using conductivity reconstruction of the presently disclosed technology, in accordance with one embodiment of the present disclosure.

In one example, Motion Tape sensors may be fabricated by integrating a sprayable GNS-based thin film with commercially available K-Tape. The GNS used, in some embodiments, may be synthesized using water-assisted liquid-phase exfoliation, and the ink and film formulation. To start, poly(vinyl alcohol) (PVA) may be slowly added to boiling deionized water and stirred at 300 rpm to make a 5 wt. % solution. Upon cooling of the solution to room temperature, a 0.1 wt. % GNS-PVA mixture may be prepared and then dispersed by subjecting it to 1 h of high-energy probe-sonication (150 W, 22 kHz). Then, the GNS-PVA solution may be sprayed using a Paasche airbrush operated at 30 psi and onto masked commercial K-Tape to form rectangular thin films on the substrate. Conductive threads were sewn at opposite ends of the GNS-PVA sensing element to form the electrodes. In addition, colloidal silver paste may be also applied over the conductive threads and film to reduce contact impedance (FIG. 6).

Figure 17:
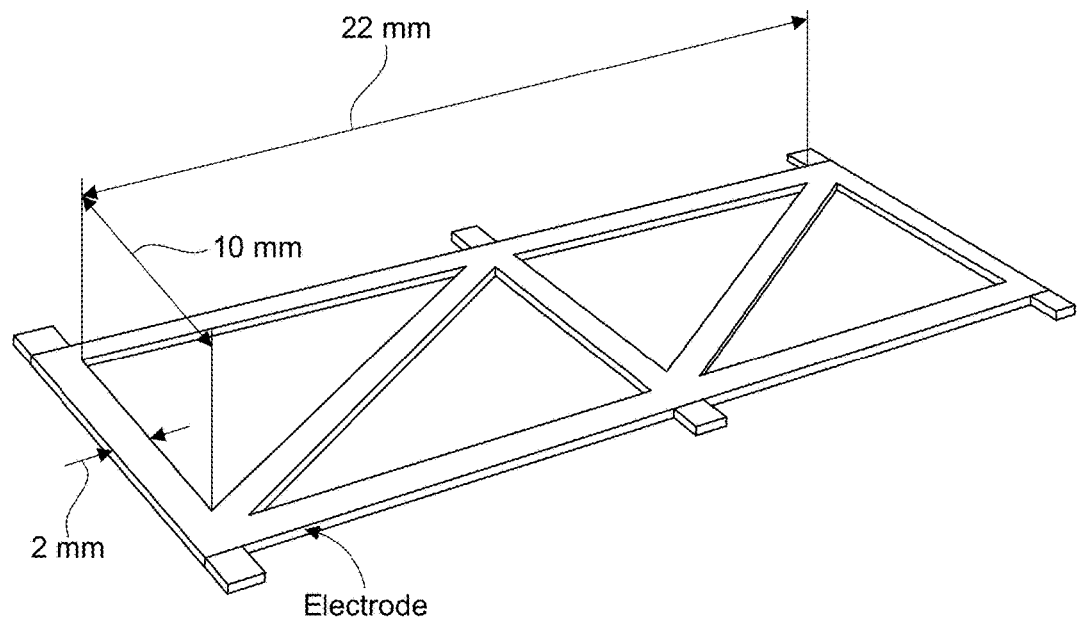
FIG. 17 illustrates an example Motion Tape sensing mesh, in accordance with one embodiment of the present disclosure. For example, the dimensions of the sensing mesh specimen are shown.
Figure 18:
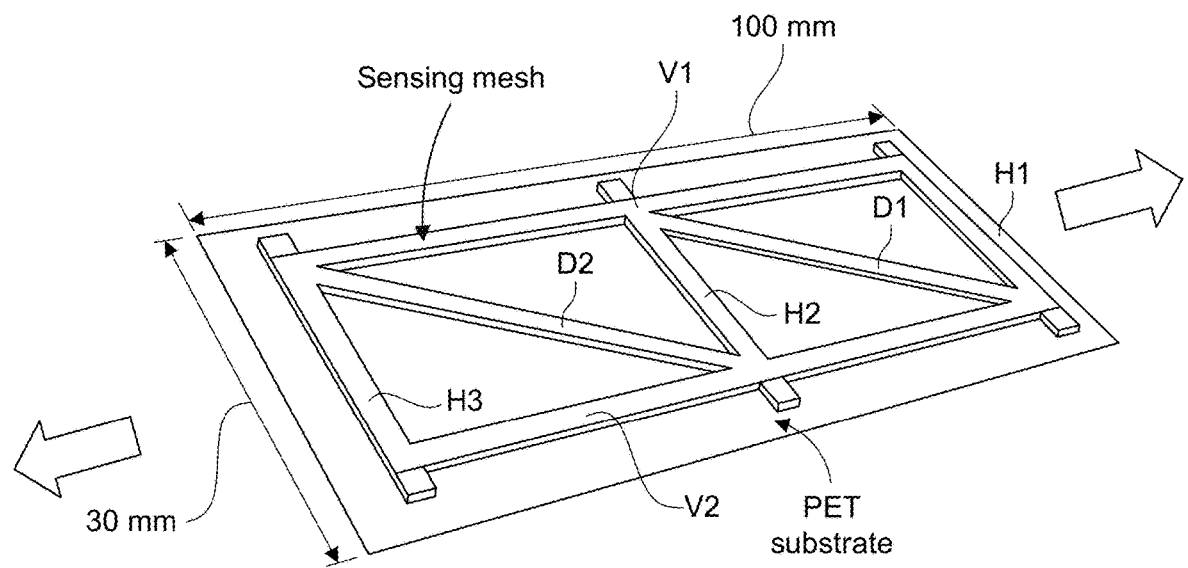
FIG. 18 illustrates an example Motion Tape sensing mesh affixed onto a PET strip and subject to uniaxial loading, in accordance with one embodiment of the present disclosure. For example, the sensing mesh may be affixed onto a PET strip and subjected uniaxial loading or affixed onto the human body for motion measurements. H, V, and D indicate the horizontal, vertical, and diagonal struts, respectively.

In another example, fabrication of the sensing mesh began by dispersing graphene nanosheets (GNS) in poly(vinyl alcohol) (PVA) solution. A laser cutter (Orion Motor Tech) may be used for patterning and forming the polyethylene terephthalate (PET) substrates to form a grid-like pattern. The GNS-PVA solution may be spray-coated onto PET grids to form the sensing mesh (FIG. 17). Conductive threads were used as electrodes and were attached to the sensing mesh using colloidal silver paste. Then, the sensing mesh may be affixed onto a 100×30 mm2 PET strip using quick-curing superglue (FIG. 18). After the glue fully cured, the PET strip with the sensing mesh may be mounted in a Test Resources 150R load frame, at which point, an initial baseline EIT dataset may be recorded (corresponding to $0\mu\varepsilon$). The load frame then applied monotonic uniaxial tensile strain to $6,000\mu\varepsilon$ at a fixed strain rate of $1,000\mu\varepsilon$/min. The load frame may be manually paused every $1,000\mu\varepsilon$ for EIT interrogations.

In one example, a graphene-based thin film of high strain sensitivity may be fabricated. The nanocomposite films may be deposited onto laser-cut patterned polyethylene terephthalate (PET) substrates using spray coating to form the sensing meshes. Each strut of the sensing mesh may be designed to have a high aspect ratio, thereby forming an interconnected equivalent network of uniaxial linear distributed strain sensors. In some embodiments, an EIT algorithm may be implemented for reconstructing the spatial conductivity distribution of the sensing mesh.

To provide some context, the mathematical background of EIT is provided herein. Upon confirming the enhanced strain sensing response of the graphene-based films, the sensing mesh may be experimentally validated to measure distributed strain fields. As further validation, the sensing mesh may be also employed to measure spatial strain distributions of different structural surfaces subjected to different levels of tensile loading. Finally, the sensing mesh may be demonstrated for its ability to monitor different damage states in a seven-story reinforced-concrete (RC) structure subjected to shaking table tests.

EIT Background

EIT is a soft-field imaging technique, where the electrical conductivity distribution of a conductive body is reconstructed from a limited number of boundary voltage measurements. EIT has been successfully used in the biomedical domain for detecting anomalies inside the human body through reconstructed conductivity maps. More recently, EIT has been adopted for applications in SHM. In general, electrodes are arranged along the perimeter of the conductive object. A direct current (DC) is applied to a pair of boundary electrodes, while the voltage drops are recorded at all remaining boundary electrodes. This excitation—measurement pattern is repeated for all boundary electrodes. An inverse problem is then solved based on this input—output relationship to reconstruct the conductivity distribution of the conductive body.

In essence, EIT includes forward and inverse problems. The forward problem is employed to estimate the electrical voltage distribution at the boundary electrodes, while the electrical excitation and conductivity distribution are known a priori. However, for experimental implementations, the EIT inverse problem is solved for reconstructing spatial conductivity from the measured set of boundary voltage responses. Both the EIT forward and inverse problems are briefly discussed herein.

EIT Forward Problem

As mentioned earlier, the EIT forward problem is solved to estimate the boundary voltage distribution of a conductive body ($\Omega$) with an explicitly known electrical conductivity distribution ($\sigma$). Mathematically, the EIT forward problem can be described by the two-dimensional (2D) Laplace's equation as shown in equation (1)

$$\nabla \cdot (\sigma \nabla u) = 0 \qquad (1)$$

where u is the electrical potential distribution in Ω. In general, a finite element model (FEM) is used to solve equation (1) with boundary conditions known as the complete electrode model. In many cases, Ω is modeled as a simple 2D plate and discretized using linear triangular or bi-linear quadrilateral elements.

In embodiments, the sensing meshes are patterned grid-like piezoresistive networks. Because of the high aspect ratio of each "strut" in the sensing mesh, induced strains in each strut are confined along their longitudinal axes, experiencing uniaxial tensile or compressive strains. This is analogous to the axial elements that make up a truss structure. Therefore, the same idea is adopted to capture the uniaxial changes in the conductivity of each strut in the sensing mesh. However, this also may use a different FEM implementation for EIT spatial conductivity mapping. In some embodiments, the high aspect ratio of each strut and the entire sensing mesh may be modeled as a 2D truss structure discretized using one-dimensional (1D) linear bar elements. By doing so, the computational cost to solve the forward problem, as well and the sensitivity matrix (J), may be significantly reduced. A reduction in the size of the sensitivity matrix eases its inversion during the execution of the inverse problem. In addition, a point electrode model may be implemented; the specified boundary conditions are shown in equation (2)

$$\sigma \frac{\partial u}{\partial n} = f \text{ on } \Gamma \qquad (2)$$

$$f = \sum_{i=1}^{M} I\delta_{s_i}$$

where I is the magnitude of current injected into Ω during EIT interrogation, Γ is the boundary of Ω, M is the number of boundary electrodes, n is the outward unit normal at the boundary, and δxi is the Dirac delta function on γ supported at xi. A boundary condition (i.e. u=0) should also be imposed on the electrode that is grounded during electrical excitation. A weak form of equation (1) may be derived by multiplying it with a sufficiently smooth test function (φ) and integrating over Ω as shown in equation (3)

$$\int_\Omega \sigma \nabla u \cdot \nabla \varphi d\Omega = \int_\Gamma \int \varphi d\Gamma \qquad (3)$$

Then, a set of linear equations obtained from equation (3) are solved to obtain u at each node of the discretized Ω.

Inverse Problem

The EIT inverse problem may reconstruct the conductivity distribution using an experimentally measured set of boundary voltage responses. A single-step linear inverse solver with Tikhonov regularization may be used to estimate the conductivity change (Δσ) from the observed change in boundary voltage distribution (ΔV) between two states $$\Delta\sigma = (J^T J + \alpha^2 I)^{-1} J^T \Delta V \qquad (4)$$

where α is the regularization parameter, and I is the identity matrix. In some embodiments, the sensitivity method may be adopted to compute J. Each term of J (i.e. Jkn), which is the derivative of the measured boundary voltage with respect to the conductivity of each finite element (FE) voxel, is evaluated using equation (5)

$$J_{lka} = \frac{\partial U_l^k}{\partial \sigma_n} = \int_{L_n} \nabla u_j \cdot \nabla u_k \, dl \qquad (5)$$

where ul and uk are the voltage distributions when the lth and kth current patterns are used, respectively. Ln is the length of the nth FE, σn is the conductivity of the nth FE, and uk/l is the kth measured boundary voltage when the lth excitation pattern is used. More details of the EIT theory and implementation can be found in other studies.

Aim #2—Distributed Physiological Monitoring

Wearable sensors may be used as discrete (point) sensors for measuring linear extension and compression, as well as angular movements. The use of multiple electrodes instrumented along the strip of the nanocomposite sensing element may enable linear (1D) distributed strain monitoring. In some embodiments, a tomographic measurement strategy and algorithm may be implemented for real-time distributed (2D) strain sensing. In some embodiments, distributed sensing along major muscle groups may be achieved using patterned nanocomposite wearable sensors and a modified electrical impedance tomography (EIT) method.

The Motion Tape and smart tattoo sensors discussed herein may be interfaced with bridge circuits and used as discrete (point) sensors. The previous electro-mechanical tests have revealed their strain sensing properties when subjected to controlled tensile cyclic loading. In embodiments, the wearable sensors may be subjected to more complex motions, such as bending and twisting to characterize their sensing response. In one example, a test fixture that resembles a surrogate human joint may be fabricated by casting a rectangular elastomer block. Two rigid 3D-printed polylactic acid (PLA) blocks may be jointed to opposite ends of the soft and flexible elastomer block to form a freely rotating joint. Motion Tape and smart tattoos may be affixed onto the surrogate joint for testing. The surrogate joint may be held in place at one end, while controlled lateral displacements may be applied at the other end to induce bending. Bending angle measurements may be acquired by video recording and image processing, and the results may be correlated with wearable sensor electrical resistance measurements. In some embodiments, torsional strains may also be applied to the wearable sensors by inducing torsion at the free end of the surrogate joint using a customized rotational test apparatus. The resistance of the Motion Tape and smart tattoos mounted in different orientations with respect to the joint may be captured and compared to strains as determined by a corresponding ABAQUS FE model.

Linear distributed strain sensing may be based on acquiring resistance measurements at multiple points along the length of the nanocomposite sensing element. Unlike mechanical- and electrical-based transducers, such as strain gages, that can acquire measurements at its instrumented location, the GNS nanocomposites may be sensitive to strain at every location in the material. This suggests that the Motion Tape sensors can make for an ideal sensing candidate for applications when multiple measurements of strains or motions are along an entire muscle group. The feasibility of this measurement modality may be tested by instrumented Motion Tape specimens with multiple conductive thread electrodes along its entire length (FIG. 6). These specimens may be affixed onto stretchable polymer substrates and loaded using a load frame to verify distributed strain sensing. Smaller-scale specimens may be fabricated and affixed onto the surrogate joint to validate distributed bending strain monitoring. Larger Motion Tape may also be mounted on a plastic beam and subjected to three-point bending using a load frame. The linear distributed strain sensing results may be compared with strain gage measurements (i.e., for uniaxial loading and three-point bending tests) and video recording data (i.e., for surrogate joint tests).

Spatial or two-dimensional (2D) sensing may be achieved by implementing an EIT measurement strategy and algorithm, whereby voltage measurements acquired along the boundary of the sensing element may be used to reconstruct the 2D resistivity (or, equivalently, strain) distribution of the entire sensing element (FIG. 1). The EIT algorithm includes the forward and inverse problems. The forward problem may solve boundary voltages based on a known resistivity (or conductivity) distribution, which is typically done so using an FE model of the conductive body. As for the inverse problem, the goal may be to reconstruct the actual conductivity distribution using experimental boundary voltage data when a pair of electrodes are used for injecting a direct current (DC) electrical excitation (FIG. 1). Multiple current injection patterns and corresponding boundary voltage responses may be acquired and used as inputs for solving the EIT inverse problem. The inverse problem (including regularization) may iterate to minimize differences between experimental voltage measurements and forward problem calculated voltage responses based on an assumed or updated conductivity distribution. In embodiments, the sensing element of Motion Tape may be instrumented with a set of boundary electrodes similar to FIG. 1. For example, an EIT algorithm may be implemented in MATLAB, and the method may be employed for demonstrating spatial sensing. Experimental validation may be performed using the aforementioned surrogate joint. Bending and torsional tests may be conducted, while boundary voltage data are acquired using a National Instruments (NI) data acquisition (DAQ) system. In addition, Motion Tape may also be mounted on foam substrates, and pressure sensing tests may be conducted by applying controlled loads and contact areas at different positions. The spatial sensing performance may be assessed objectively using established metrics, such as by computing position error, area ratio, and resolution.

A highly flexible and adaptable distributed sensing method may be disclosed herein, where the sensing region is defined by a connected mesh-like network of Motion Tape. In some embodiments, the ability of EIT may be expanded to not only capture distributed strain magnitudes but also their strain directionalities. Strain directionality can be captured, because each Motion Tape, with its high aspect ratio nanocomposite sensing element, effectively serves as a 1D linear distributed sensor. EIT may be able to capture the magnitudes of strains captured along its length, with its direction aligned with the longitudinal axis of each sensing element. Two electrodes may be formed at opposite ends of the high aspect ratio sensing element. Each electrode may be formed by sandwiching two small pieces of ultra-thin copper tape with the Motion Tape in the middle and then sewing the tapes together using conductive threads. These specialized electrodes are used to connect (electrically) multiple Motion Tape pieces at these nodes. In some embodiments, various grid-like Motion Tape meshes may be prepared by connecting individual Motion Tape specimens at its nodes to form a patterned network (e.g., a rectangular grid). Electrodes may also be formed along the boundaries of the defined meshes for EIT data acquisition. In some embodiments, a modified EIT algorithm that leverages 1D elements in the FE model of the forward problem may be implemented. The distributed sensing performance of Motion Tape meshes may be validated by mounting them onto large stretchable polymer substrates and subjected to different load patterns. The EIT results may be compared to expected strains based on FE simulations. In addition to Motion Tape meshes, small-scale patterned nanocomposite meshes may also be printed on the smart tattoos. These smart tattoo meshes may also be mounted and tested using the surrogate joint as they are subjected to bending and torsional load scenarios.

A laser cutter may be employed to pattern PET sheets to form a complex mesh geometry. Then, strain-sensitive GNS-PVA thin films may be spray-coated onto the patterned PET sheets and dried to form the sensing mesh. The specimen may be epoxy-mounted onto a continuous PET substrate and then loaded in a Test Resources 150R load frame for testing. Uniaxial tension may be applied, and EIT may be performed at pre-defined strain states to capture the distributed sensing response of the film.

The Motion Tape sensors may be validated for characterizing human motions. Motion Tape specimens were adhered onto the upper arm of a subject, and the subject curled and uncurled her arm for numerous cycles, which resulted in the bicep muscles to contract and expand during this test (FIG. 8). FIG. 8 shows that the Motion Tape resistance decreased when the arm may be curled (i.e., when the bicep muscles contracted), and the opposite may be true when the arm may be uncurled and relaxed. This result may be expected, since contraction of the bicep muscles would induce local compression of the skin in that area, even though that section of the upper arm physically becomes thicker. It can also be observed from FIG. 8 that the Motion Tape specimen demonstrated relatively stable and repeatable behavior.

In embodiments, a low-cost, low-profile, and high-performance wearable strain sensor may be fabricated by depositing GNS-PVA thin films directly onto commercial K-Tape. The electromechanical properties of the Motion Tape specimens were characterized, and it may be found that its resistance increased in tandem with increasingly applied tensile strains. Its average gage factor may be calculated to be ~28. The last set of tests validated the use of Motion Tape for human motion monitoring. Motion Tape may be adhered on a subject's arm, and the sensor's performance may be characterized as the subject performed repetitive motions (i.e., curling and contracting/relaxing the bicep muscles). The results showed that the sensor may be able to capture the subject's arm motions, and the sensing response may be fairly stable and repeatable. In the near future, the Motion Tape specimens may be attached onto different parts of the body for characterizing its ability to quantify different types of human motions and activity.

In some embodiments, a GNS-based thin film sensing mesh may be coupled with EIT for distributed strain field monitoring. The test results showed that EIT may be able to identify if any of the struts in the sensing mesh may be subjected to tension or compression, as well as the corresponding magnitude and directionality of strain. The EIT-estimated strains were compared with FE analysis for verification, and good agreement may be observed. Future work may consider more complex sensing mesh designs and different load patterns.

In embodiments, distributed strain field monitoring may be accomplished using a patterned nanocomposite "sensing mesh" that is coupled with an electrical impedance tomography (EIT) measurement strategy and algorithm. Although EIT has been used in other studies and in conjunction with a piezoresistive thin film for spatial damage detection, different strain components cannot be directly extracted from reconstructed EIT conductivity maps. In embodiments, patterning piezoresistive graphene-based thin films are used to form a mesh-like pattern. The high aspect ratio of each nanocomposite grid interconnect acts as a linear distributed strain sensor, capable of resolving strains along the entire length and direction of the element. In some embodiments, the strain-sensitive film may be spray-coated onto patterned polymer substrates to form the sensing meshes, which were then subjected to load tests. Upon validating distributed strain field monitoring through EIT, its applicability for field implementation and damage characterization may be also demonstrated by instrumenting sensing meshes onto structural surfaces. The test results successfully validated distributed damage detection.

In one example to achieve distributed strain field monitoring, a nanocomposite thin film may be designed and fabricated, whose electrical conductivity (or resistivity) may be sensitive to applied strains and deformation. Among the variety of nanomaterials that are available today, a significant body of current research focuses on the graphene nanosheet (GNS), which exhibits outstanding intrinsic properties, with piezoresistivity being just one of them. For example, the Young's modulus of a single-layer graphene sheet could be as high as 1 TPa with a gage factor of 11.4. Several studies already showed that GNS could be integrated into polymer matrices to form high-performance strain sensors.

The GNS used may be synthesized using water-assisted liquid-phase exfoliation. The process began by mixing microcrystalline graphite powder with an aqueous solution of N-methyl-2-pyrrolidone (NMP), followed by 6 h of bath sonication at a fixed nominal power (100 W) and frequency (37 kHz). Thereafter, the sonicated graphene-NMP solution may be centrifuged at 3000 r/min for 30 min. The upper 75% of the centrifuged colloidal solution (i.e. the supernatant) may be collected and then dried to obtain agglomerated GNS. The GNS-based thin film strain sensor may be then fabricated by dispersing them in an ethyl cellulose (EC) solution. The GNS-EC ink fabrication process is discussed herein.

Figure 14:
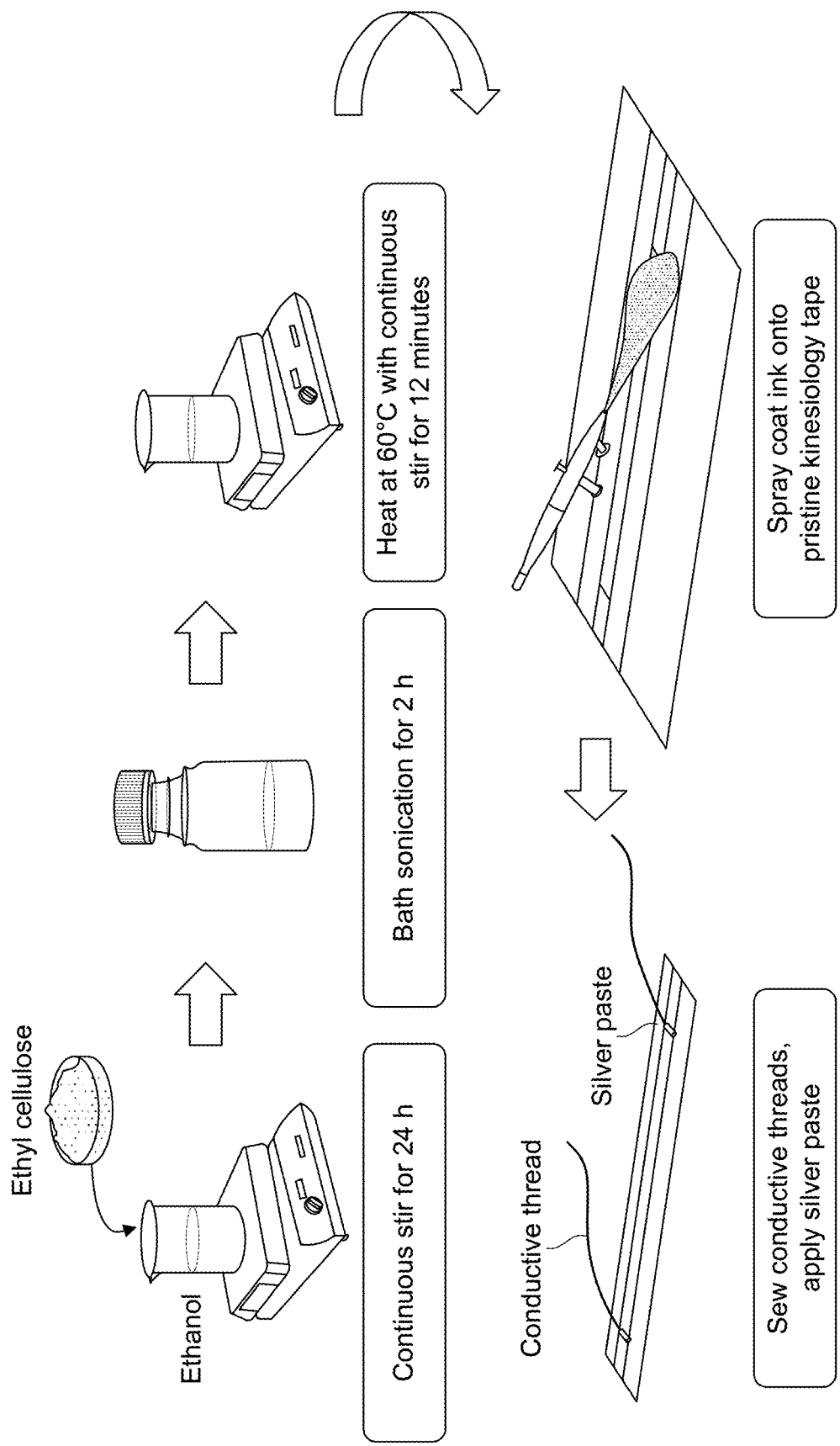
FIG. 14 illustrates an example method of preparing GNS-based ink in ethyl cellulose (EC) and spray fabrication, in accordance with one embodiment of the present disclosure.
Figure 15:
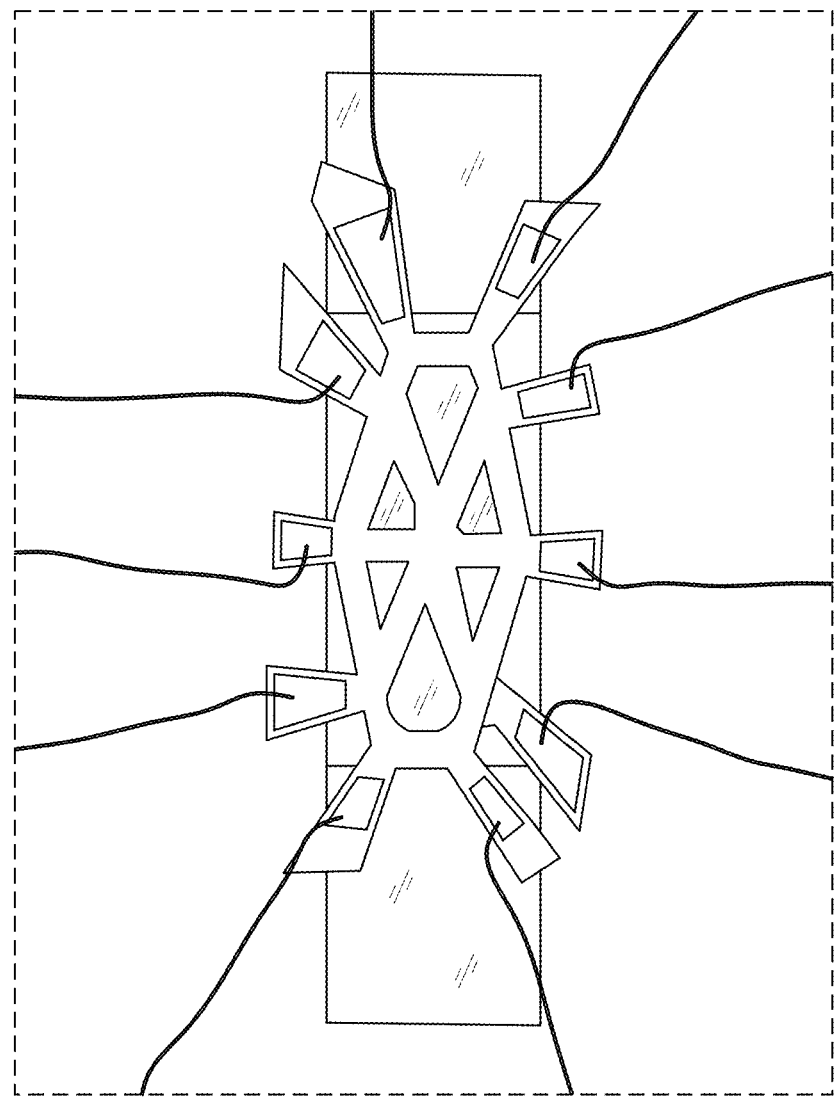
FIG. 15 illustrates the presently disclosed technology cut into grid-like patterns using a cutter that is mounted in a load frame and subjected to tensile cyclic loading. EIT measurements were acquired at different strain states, while the load frame may be paused, in accordance with one embodiment of the present disclosure.
Figure 16:
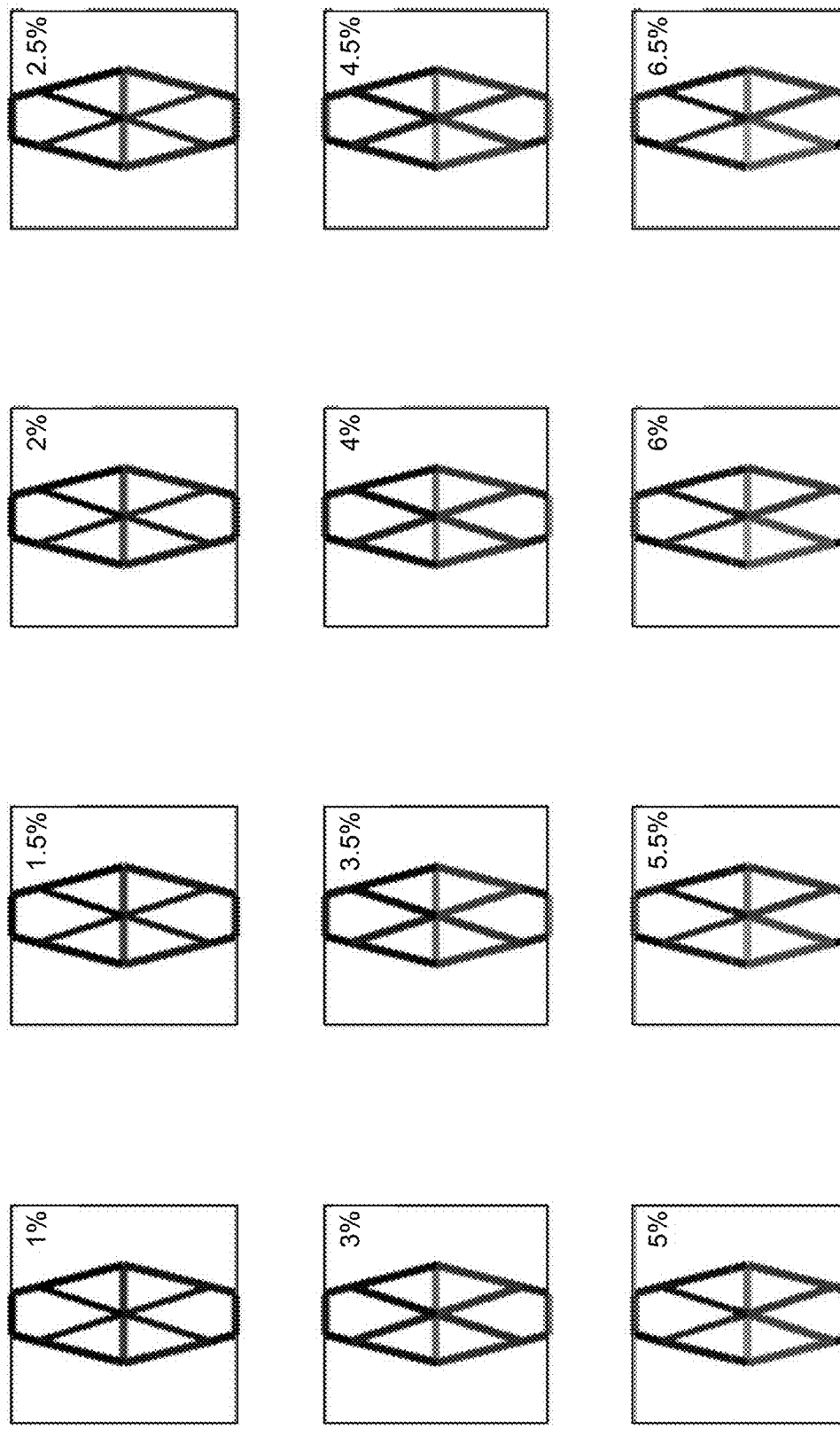
FIG. 16 illustrates EIT conductivity tests on a sensing mesh, in accordance with one embodiment of the present disclosure.

FIG. 14 illustrates an example method of preparing GNS-based ink in ethyl cellulose (EC) and spray fabrication, in accordance with one embodiment of the present disclosure. Ethyl cellulose (EC) was added to 200 proof ethanol to obtain a 2 wt. % EC-ethanol solution. The mixture was then subjected to 24 h of continuous stirring using a magnetic stirrer. Upon complete dissolution of EC, GNS was added to the EC-ethanol solution at a concentration of 15 mg/mL. GNS dispersion was achieved by bath sonication for 2 h (150 W, 22 kHz). Next, the viscosity of the solution was adjusted by heating it on a digital hotplate to 60° C. for ~12 min while allowing a portion of the ethanol to evaporate. The sprayable GNS-EC ink was obtained upon cooling the solution back to room temperature.

Spray fabrication may be adopted because one could produce high-quality and large-scale GNS-EC thin films quickly. Although a manual deposition procedure may be employed in this work, spraying can be fully automated through the use of robotic spray systems. Furthermore, spraying is beneficial as one can directly deposit films onto various (and masked) structural surfaces, thereby eliminating problems associated with gluing sensing meshes and issues regarding nonuniform strain transfer from the structural surface to the sensing element.

Aim #3—Portable and Field-Deployable Measurements

A highly conductive ink may be used for forming electrodes and in lieu of colloidal silver paste. In some embodiments, a miniature, portable, and wireless EIT DAQ node may be used. In some embodiments, signal processing algorithms may be embedded as firmware in the microcontroller of the portable DAQ unit to facilitate high quality measurements and pre-processing of raw data.

Electrically conductive ink formulations may be utilized for forming wearable sensor electrodes, which may also be deposited using the same fabrication methods used for forming the GNS-based sensing elements. Doing so may result in a streamlined approach for depositing the nanocomposite thin films and conductive electrodes using a consistent fabrication methodology to ensure strong bonding and chemical compatibility. The conductive ink formulations may be prepared based on the GNS ink formulations as discussed herein. GNS may be replaced with carbon nanotubes, silver (Ag) nanoparticles (NP) or carbon black (CB). The dispersion of Ag NPs and CB in the polyelectrolyte solutions may be investigated, optimized, and assessed via optical techniques. Dried conductive films may also be evaluated using scanning electron microscopy (SEM) and subsequent image processing to characterize the density of conductive species deposited. Electrical impedance spectroscopy may be used to measure their electrical conductivity. Subsequent iterations to improve conductivity may be performed by adjusting Ag NP and/or CB concentration and by means of post-film thermal annealing for densifying the films.

Figure 19:
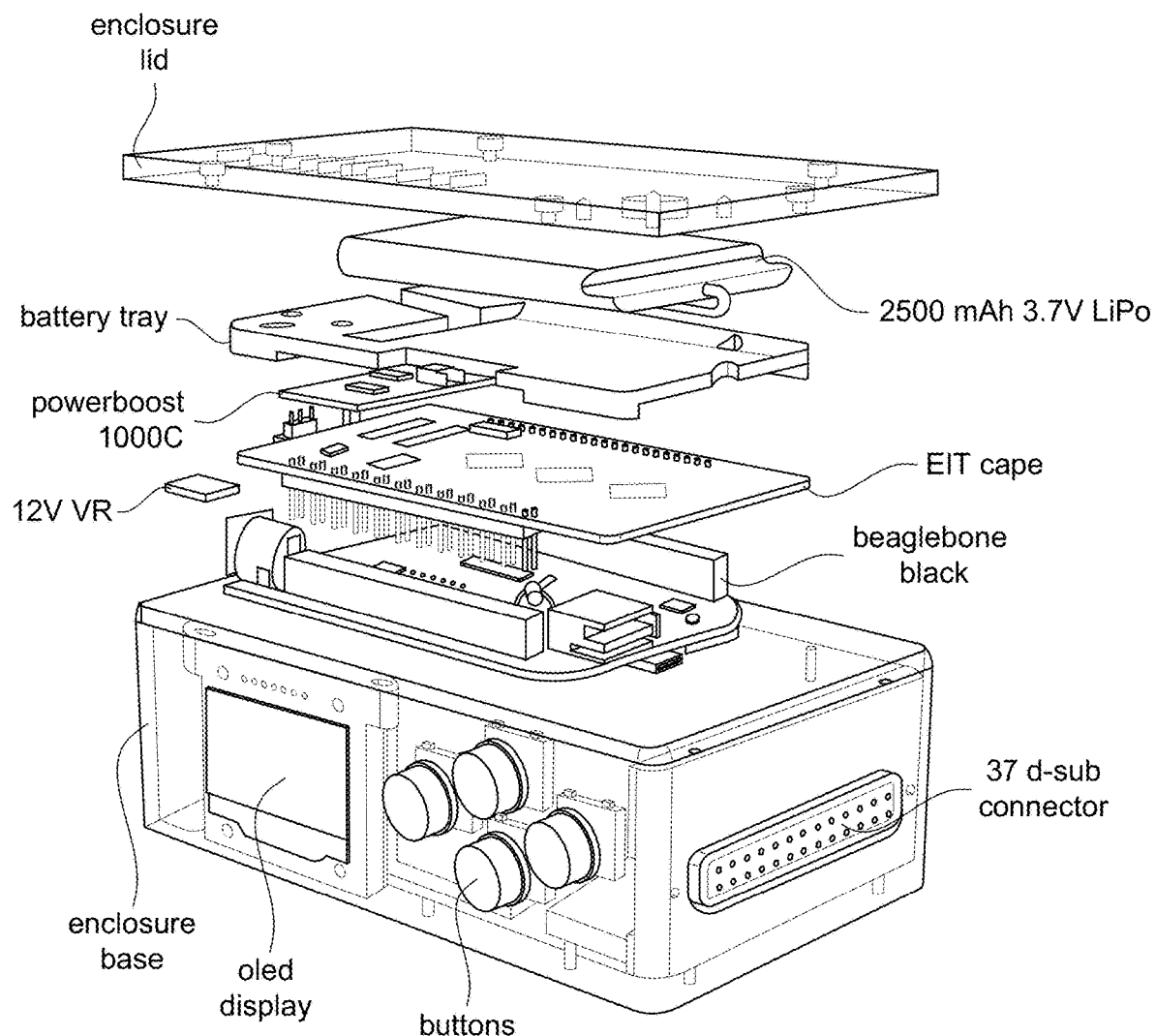
FIG. 19 illustrates an example portable measurement unit concept, in accordance with one embodiment of the present disclosure.

A portable and miniature wireless data acquisition node powered by a BeagleBone-like developmental platform may be used for interrogating the wearable sensors, locally processing sensor signals, and transmitting data/results to a remote base station. The goal is to create a portable DAQ system to facilitate human subject testing and to help transition this technology. In so far, wearable sensor measurements would be acquired using digital multimeters (DMM) (i.e., for two-point probe resistance measurements) or an NI DAQ system (i.e., for tomographic measurements); both these systems are too bulky for human testing and field applications. Thus, the electrical subsystem responsible for data collection and processing may be considered, which may include the software system that controls the electronic hardware, and the mechanical enclosure. First, the BeagleBone Black developmental board may be employed as the backbone system that powers this unit. BeagleBone Black is selected because of its built-in 1 GHz processor, as well as its wide range of serial and 69 configurable GPIO interfaces. In addition, a board that houses multiplexors, current source, current sensor, and analog-to-digital converters (ADC) may be fabricated so that it sits directly on top of the BeagleBone Black board and connects via its existing interfaces. An internal lithium ion battery may also be included to power the system for extended use (FIG. 19). In some embodiments, a customized operating system software may be implemented in C to control the entire unit. The software may allow the user to select whether multiple resistance measurements are desired or if different current injection/measurement patterns should be used for acquiring EIT datasets. Finally, the external enclosure of the portable unit may be custom made by 3D printing. This research-grade unit may primarily be used in laboratory conditions, so no effort may be made to waterproof or shockproof the system. Rather, the enclosure secures all the components together in a compact form factor and allows for ease of testing in various conditions (FIG. 19).

Signal processing algorithms may be implemented and embedded as firmware in the BeagleBone Black computational core for local data processing and conditioning. With most wireless sensing systems limited to using 16-bit ADCs, it is expected that the portable DAQ system may employ similar ADCs in order to achieve an optimal balance between raw data resolution and sampling speed. Therefore, to compensate for its lower resolution (as compared to the NI DAQ system), signal amplification, filtering, and denoising schemes may be leveraged to enhance data quality. These signal processing toolboxes programmed in C may be used to post-process the digitized voltage measurements. First, a low-pass filter may be implemented to remove high-frequency noise (e.g., due to electrical noise present in such a compact system). In some embodiments, a smoothing algorithm based on a moving average may also be applied for noise reduction. Depending on the actual sampling rates used and parameters for the results, down-sampling can also be performed to further reduce noise. Finally, low-amplitude signals (e.g., as a result of highly conductive or small films, such as the smart tattoos) may be digitally amplified. Overall, the objective is to encode a suite of signal processing tools for allowing the user to select the most appropriate ones depending on testing conditions and the sensors used.

Aim #4—Sensor Testing, Validation, and Optimization

To summarize other details disclosed herein, all specimens may be subjected to tensile cyclic load tests while their electrical properties are recorded and analyzed. Strain sensing properties, such as their strain sensitivity, resolution, accuracy, root-mean-square noise floor, linearity, and hysteresis, may be determined. The Test Resources 150R and 100R load frames may be used to apply monotonic uniaxial tensile and tensile cyclic loads to the specimens. Input excitation (i.e., applied load and crosshead displacement) may be recorded using Keysight Benchvue, as well as the electrical measurements, so that all data streams are time-synchronized. It should be mentioned that this load frame can be configured with different grip setups to accommodate uniaxial compressive tests and three-point bending tests. Electrical measurements may be acquired using Keysight 34465A DMMs. On the other hand, EIT tests may be conducted using a customized NI DAQ system or a Keysight 34980A multifunctional switch equipped with an embedded DMM, where electrical current excitations may be supplied by a Keithley 6221 current generator. Customized MATLAB and LabVIEW programs are readily available to control these instrument suites via software.

The subjects may be instrumented with the wearable sensors at different locations on their body. Motion Tape may be affixed over major muscle groups (e.g., biceps, pectorals, latissimus dorsi, gastrocnemius, back, and quadriceps), whereas smart tattoos may be instrumented near joints (e.g., ankles, knees, elbows, and neck). In some embodiments, subjects with wearable sensors may be asked to perform simple and controlled motions in the laboratory. These motions include bending a joint to predefined angles/positions, as well as stationary weight training activities (e.g., push-ups, vertical jumps, bicep curls, squats, and lunges, among others). Different weights may be used to purposefully change the level of effort to perform certain motions. In addition, the subject's motions may be captured via video so that image processing of individual image frames can be performed to quantify the relative positions of different body parts. Finally, the subjects may undergo higher-activity-level fitness activities such as walking, jogging, and running on a treadmill, while sensor measurements are acquired. In the initial stages, laboratory equipment (e.g., DMM and NI DAQ) may be used to acquire sensor data in the laboratory. When the portable measurement node is tested, it may be used for later stages of testing and when subjects engage in higher-activity-level activities. A diverse subject pool may be considered, but a few subjects may be recruited, since this is not a clinical trial. Furthermore, Institutional Review Board (IRB) human subject testing approval was requested and approved through the UC San Diego Human Research Protections Program.

The initial Motion Tape and smart tattoos may ensure that high quality human motion data can be captured. The analysis of wearable sensor properties during the various laboratory characterization and human subject tests may probably reveal issues that should be addressed in later iterations of sensor design. For example, the connection between conductive thread and wearable sensors has been found to be susceptible to damage and failure. The electrodes can be reinforced by sandwiching the electrodes in fabric-like iron-on adhesives to prevent them from detaching as the subjects move. Another possibility is enhancing sensor sensitivity. The GNS solution and ink formulations may be optimized to find the ideal GNS and polymer matrix concentrations that yield the highest sensing performance. Additional optimization parameters may continue to be considered throughout the entire project.

Testing

In one example, the strain sensing properties of Motion Tape sensors were characterized by subjecting them to monotonic uniaxial tensile loading (using a Test Resources 100R load frame) while simultaneously recording their electrical resistance. Each specimen may be loaded to a maximum strain of 72.5% at a constant displacement-controlled rate of 5%/min. Electrical resistance may be measured using a Keysight 34465A digital multimeter recording data at a sampling rate of 2 Hz. FIG. 6 shows that, with increasing applied tensile strains, the electrical resistance increased as well. From FIG. 6, the strain sensitivity or gage factor may be calculated to be ~28.

One of the most widely used strain measuring instruments is a foil-based strain gage that is directly attached to the structural surface of interest. Despite their low cost, high accuracy, and high resolution, they are discrete sensors that may be densely instrumented for quantifying the strain distribution of a structural component. On the other hand, fiber Bragg grating (FBG) sensors offer several advantages versus other electronic-based strain transducers (e.g. fast response, resistance to corrosion, and immunity to electromagnetic noise and radio frequency interference). The ability to multiplex and measure strains at different locations is another major advantage. However, complex and expensive equipment is used to interrogate FBGs, and their high manufacturing and installation costs are impediments to practical use.

The strain sensing properties of the GNS-EC thin films were characterized by conducting tensile cyclic tests, as discussed herein. The thin films' resistance may be measured throughout testing, as may be the applied strains. A peak tensile strain of 5000µε may be applied to the specimens so that the films remained undamaged and linear elastic.

Figure 5:
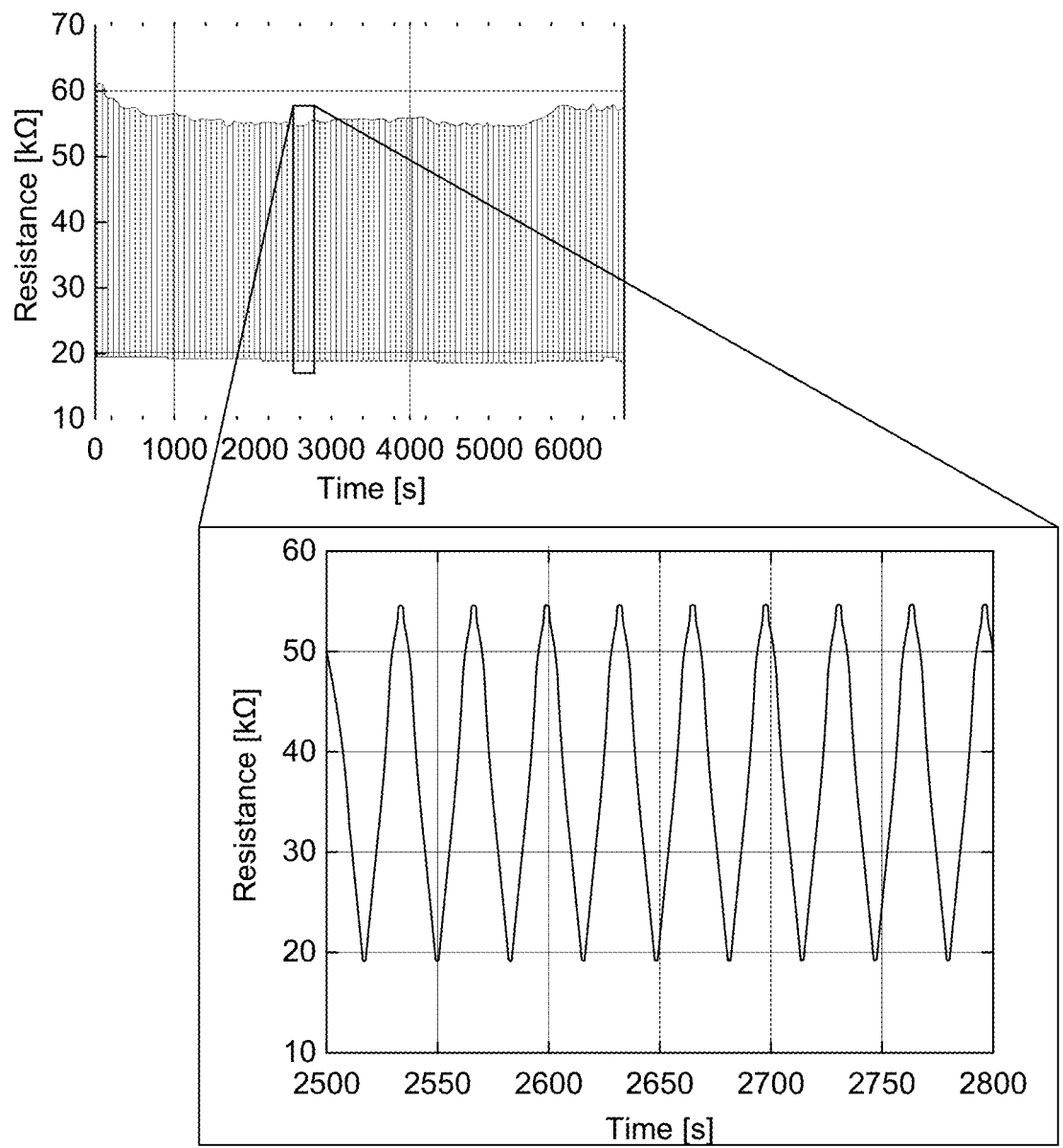
FIG. 5 illustrates test data relating to FIG. 4, in accordance with one embodiment of the present disclosure.

FIG. 5 shows a representative GNS-EC thin film's resistance response when subjected to tensile cyclic testing. This result confirmed that the resistance of the thin film changed in tandem with applied strains. In addition, its electromechanical response may be stable and repeatable. Furthermore, the same set of data may be used to plot the normalized change in resistance versus strain, as shown in FIG. 6. A linear least-squares regression line may be fitted to estimate their gage factor (G) or strain sensitivity (i.e. the slope of the fitted line)

$$G = \frac{\Delta R/R_0}{\Delta \varepsilon} \qquad (6)$$

where R0 is the initial or unstrained resistance of the thin film, and ΔR is the change in resistance with respect to R0 when strain (Δε) is applied.

The presently disclosed technology may be used for health management. The "human twin" and its digital twin would constitute a mutually interacting cyber-physical-human system to assess and mitigate MSK injury risks, with the goals of maximizing warfighter performance, minimizing risk of injuries, and enabling rapid and active rehabilitation (for those recovering from MSK injuries). The digital twin is an individualized cyber representation of the warfighter to acquire, aggregate, fuse, and analyze diverse data streams to: (1) assess current well-being; (2) predict future health based on different possible decisions/actions; and (3) deliver effective interventions that change human behavior to improve wellness. The digital twin may be born and evolve with its warfighter twin, as it is continuously updated with purposefully acquired sensory, physiologic, and biopsychosocial data streams, to assess and communicate health status, increase self-awareness, and deliver individualized interventions that drive positive behavioral changes and promote wellness. The capability of acquiring accurate, reliable, and representative physiologic data streams of the warfighter during training and in forward-deployed operations, which may be brought to bear by this project, is a step in obtaining the data streams that feed and support the digital twin. The digital twin may empower the Navy and each warfighter to engage in both prehabilitation—enhanced personal MSK health, well-being, and resilience—and personalized rehabilitation—rapid recovery and functionality gains post-injury.

The presently disclosed technology may include advantages versus the current state-of-the-art:
  Distributed strain/motion measurements versus discrete (one point) measurements
  Conformable sensors mounted directly onto the skin versus rigid, bulky, electronic-based sensors
  Direct measurement of muscular activity versus back-calculated from joint movements (e.g., from motion capture systems)
  Sensor fabricated on K-Tape, which is already used for physical therapy and adds value by providing quantitative measurements of motion.

The presently disclosed technology may be used in various application areas:
  Physical therapy
  Athletes/warfighter motion and physical assessment, performance monitoring, and performance enhancement
  Healthcare uses for diagnosis of diseases/disorders that present physical symptoms
  Healthcare uses for monitoring of wound healing
  Integration in commercial wearable products (e.g., for contact sports such as taekwando vests, boxing gloves, garments, etc.) or law enforcement/military protective gear (e.g., body armor)
  Distributed sensor feedback for robotics, haptic gloves, and human-machine interface systems
  Monitoring worker fatigue and potential overuse injuries
  Laboratory assessment tool for wearable systems.

Figure 20:
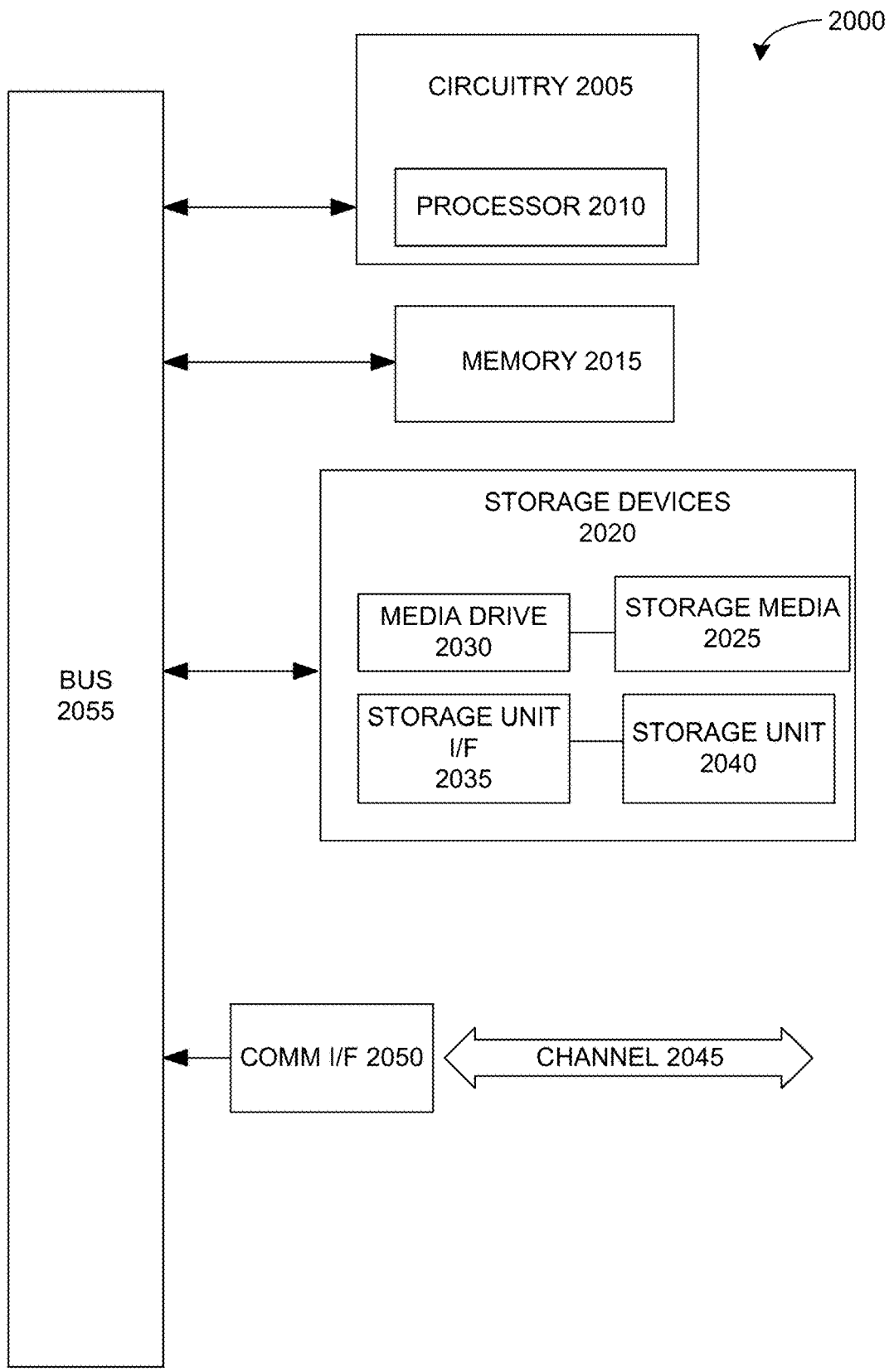
FIG. 20 illustrates an example computing component that may be used to implement features of various embodiments of the disclosure The figures are not intended to be exhaustive or to limit the presently disclosed technology to the precise form disclosed. It should be understood that the presently disclosed technology can be practiced with modification and alteration, and that the disclosed technology be limited only by the claims and the equivalents thereof.

FIG. 20 illustrates example computing component 2000, which may in some instances include a processor on a computer system (e.g., control circuit). Computing component 2000 may be used to implement various features and/or functionality of embodiments of the systems, devices, and methods disclosed herein. With regard to the above-described embodiments set forth herein in the context of systems, devices, and methods described with reference to FIGS. 1-19, including embodiments involving the control circuit, one of skill in the art will appreciate additional variations and details regarding the functionality of these embodiments that may be carried out by computing component 2000. In this connection, it will also be appreciated by one of skill in the art upon studying the present disclosure that features and aspects of the various embodiments (e.g., systems) described herein may be implemented with respected to other embodiments (e.g., methods) described herein without departing from the spirit of the disclosure.

As used herein, the term component may describe a given unit of functionality that may be performed in accordance with one or more embodiments of the present application. As used herein, a component may be implemented utilizing any form of hardware, software, or a combination thereof. For example, one or more processors, controllers, ASICs, PLAs, PALs, CPLDs, FPGAs, logical components, software routines, or other mechanisms may be implemented to make up a component. In implementation, the various components described herein may be implemented as discrete components or the functions and features described may be shared in part or in total among one or more components. In other words, as would be apparent to one of ordinary skill in the art after reading this description, the various features and functionality described herein may be implemented in any given application and may be implemented in one or more separate or shared components in various combinations and permutations. Even though various features or elements of functionality may be individually described or claimed as separate components, one of ordinary skill in the art will understand upon studying the present disclosure that these features and functionality may be shared among one or more common software and hardware elements, and such description shall not require or imply that separate hardware or software components are used to implement such features or functionality.

Where components or components of the application are implemented in whole or in part using software, in embodiments, these software elements may be implemented to operate with a computing or processing component capable of carrying out the functionality described with respect thereto. One such example computing component is shown in FIG. 20. Various embodiments are described in terms of example computing component 2000. After reading this description, it will become apparent to a person skilled in the relevant art how to implement example configurations described herein using other computing components or architectures.

Referring now to FIG. 20, computing component 2000 may represent, for example, computing or processing capabilities found within mainframes, supercomputers, workstations or servers; desktop, laptop, notebook, or tablet computers; hand-held computing devices (tablets, PDA's, smartphones, cell phones, palmtops, etc.); or the like, depending on the application and/or environment for which computing component 2000 is specifically purposed.

Computing component 2000 may include, for example, one or more processors, controllers, control components, or other processing devices, such as a processor 2010, and such as may be included in 2005. Processor 2010 may be implemented using a special-purpose processing engine such as, for example, a microprocessor, controller, or other control logic. In the illustrated example, processor 2010 is connected to bus 2055 by way of 2005, although any communication medium may be used to facilitate interaction with other components of computing component 2000 or to communicate externally.

Computing component 2000 may also include one or more memory components, simply referred to herein as main memory 2015. For example, random access memory (RAM) or other dynamic memory may be used for storing information and instructions to be executed by processor 2010 or 2005. Main memory 2015 may also be used for storing temporary variables or other intermediate information during execution of instructions to be executed by processor 2010 or 2005. Computing component 2000 may likewise include a read only memory (ROM) or other static storage device coupled to bus 2055 for storing static information and instructions for processor 2010 or 2005.

Computing component 2000 may also include one or more various forms of information storage devices 2020, which may include, for example, media drive 2030 and storage unit interface 2035. Media drive 2030 may include a drive or other mechanism to support fixed or removable storage media 2025. For example, a hard disk drive, a floppy disk drive, a magnetic tape drive, an optical disk drive, a CD or DVD drive (R or RW), or other removable or fixed media drive may be provided. Accordingly, removable storage media 2025 may include, for example, a hard disk, a floppy disk, magnetic tape, cartridge, optical disk, a CD or DVD, or other fixed or removable medium that is read by, written to or accessed by media drive 2030. As these examples illustrate, removable storage media 2025 may include a computer usable storage medium having stored therein computer software or data.

In alternative embodiments, information storage devices 2020 may include other similar instrumentalities for allowing computer programs or other instructions or data to be loaded into computing component 2000. Such instrumentalities may include, for example, fixed or removable storage unit 2040 and storage unit interface 2035. Examples of such removable storage units 2040 and storage unit interfaces 2035 may include a program cartridge and cartridge interface, a removable memory (for example, a flash memory or other removable memory component) and memory slot, a PCMCIA slot and card, and other fixed or removable storage units 2040 and storage unit interfaces 2035 that allow software and data to be transferred from removable storage unit 2040 to computing component 2000.

Computing component 2000 may also include a communications interface 2050. Communications interface 2050 may be used to allow software and data to be transferred between computing component 2000 and external devices. Examples of communications interface 2050 include a modem or softmodem, a network interface (such as an Ethernet, network interface card, WiMedia, IEEE 2020.XX, or other interface), a communications port (such as for example, a USB port, IR port, RS232 port Bluetooth® interface, or other port), or other communications interface. Software and data transferred via communications interface 2050 may typically be carried on signals, which may be electronic, electromagnetic (which includes optical) or other signals capable of being exchanged by a given communications interface 2050. These signals may be provided to/from communications interface 2050 via channel 2045. Channel 2045 may carry signals and may be implemented using a wired or wireless communication medium. Some non-limiting examples of channel 2045 include a phone line, a cellular or other radio link, an RF link, an optical link, a network interface, a local or wide area network, and other wired or wireless communications channels.

In this document, the terms "computer program medium" and "computer usable medium" are used to generally refer to transitory or non-transitory media such as, for example, main memory 2015, storage unit interface 2035, removable storage media 2025, and channel 2045. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions may enable the computing component 2000 or a processor to perform features or functions of the present application as discussed herein.

While various embodiments of the disclosed technology have been described above, it should be understood that they have been presented by way of example only, and not of limitation. Likewise, the various diagrams may depict an example architectural or other configuration for the disclosed technology, which is done to aid in understanding the features and functionality that can be included in the disclosed technology. The disclosed technology is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the technology disclosed herein. Also, a multitude of different constituent component names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the disclosed technology is described above in terms of various exemplary embodiments and implementations, it should be understood that the various features, aspects and functionality described in one or more of the individual embodiments are not limited in their applicability to the embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "component" does not imply that the components or functionality described or claimed as part of the component are all configured in a common package. Indeed, any or all of the various components of a component, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. A method comprising:
   (a) interrogating a sensing mesh using an electrical impedance tomography (EIT) device, wherein the sensing mesh is affixed onto skin nearby a musculoskeletal (MSK) region of interest, wherein the sensing mesh comprises a nanocomposite thin film disposed on elastic fabric tape;
   (b) generating EIT conductivity maps from interrogating the sensing mesh;
   (c) generating strain distribution and strain directionality data of the MSK region of interest based on the EIT conductivity maps;
   (d) generating a digital twin characterizing a MSK system of a subject using the strain distribution and strain directionality data; and
   (e) updating the digital twin to assess changes in the MSK system of the subject by repeating steps (a)-(c).

2. The method of claim 1, wherein the MSK region of interest comprises one or more of a bicep region, pectoral region, latissimus dorsi region, gastrocnemius region, quadricep region, ankle region, knee region, elbow region, back region, and neck region.

3. The method of claim 1, wherein the nanocomposite thin-film comprises one or more of a graphene nanosheet, carbon nanotube, carbon black, and silver nanoparticles.

4. The method of claim 1, wherein the sensing mesh comprises conductive threads, fibers, or wires electrically coupling edges of the sensing mesh together.

5. The method of claim 1, wherein disposing the nanocomposite thin film on the elastic fabric tape comprises one or more of spray-coating, screen-printing, inkjet printing, and micro plotting.

6. The method of claim 1, wherein the sensing mesh forms a geometrical pattern on the skin.

7. The method of claim 6, wherein the geometrical pattern comprises a grid.

8. A method comprising:
   interrogating a sensing mesh using an electrical impedance tomography (EIT) device, wherein:
      the sensing mesh is affixed onto skin nearby a musculoskeletal (MSK) region of interest,
      the sensing mesh comprises a graphene nanosheet (GNS) thin film disposed on elastic fabric tape, and
      synthesizing the GNS thin film comprises uniformly dispersing GNS to form stable polyelectrolyte solutions without phase segregation;
   generating EIT conductivity maps using data measured from interrogating the sensing mesh with the EIT device; and
   generating strain distribution and strain directionality data of the MSK region of interest using the EIT conductivity maps.

9. The method of claim 8, wherein the MSK region of interest comprises one or more of a bicep region, pectoral region, latissimus dorsi region, gastrocnemius region, quadricep region, ankle region, knee region, elbow region, back region, and neck region.

10. The method of claim 8, wherein the sensing mesh comprises conductive threads, fibers, or wires electrically coupling edges of the sensing mesh together.

11. The method of claim 8, wherein the elastic fabric tape is arranged in a geometrical pattern to form an interconnected network.

12. The method of claim 8, further comprising:
   generating a digital twin characterizing a MSK system of a subject using the strain distribution and strain directionality data; and
   updating the digital twin to assess changes in the MSK system of the subject by repeating the above steps.

* * * * *